(12) United States Patent
Lundahl et al.

(10) Patent No.: US 6,709,446 B2
(45) Date of Patent: *Mar. 23, 2004

(54) ILLUMINATOR FOR PHOTODYNAMIC THERAPY AND DIAGNOSIS WHICH PRODUCES SUBSTANTIALLY UNIFORM INTENSITY VISIBLE LIGHT

(75) Inventors: Scott Lundahl, Lexington, MA (US); Rebecca Kozodoy, Randolph, MA (US); Ronald Carroll, Hingham, MA (US); Elton Leppelmeier, Highland Height, OH (US)

(73) Assignee: Dusa Pharmaceuticals, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/774,084

(22) Filed: Jan. 31, 2001

(65) Prior Publication Data

US 2001/0021812 A1 Sep. 13, 2001

Related U.S. Application Data

(62) Division of application No. 09/070,772, filed on May 1, 1998, now Pat. No. 6,223,071.

(51) Int. Cl.[7] .............................................. A61N 5/06
(52) U.S. Cl. .......................................... 607/88; 607/91
(58) Field of Search ........................ 607/88–95; 600/476

(56) References Cited

U.S. PATENT DOCUMENTS

| | | | |
|---|---|---|---|
| 2,560,808 A | 7/1951 | Maccallum | 607/91 |
| 2,699,771 A | 1/1955 | Ruttger-Pelli | 128/24.1 |
| 4,100,415 A | 7/1978 | Blaisdell et al. | 250/455 |
| 4,103,175 A | 7/1978 | Levin | 250/504 |
| 4,335,724 A | 6/1982 | Frei et al. | 128/395 |
| 4,852,549 A * | 8/1989 | Mori | 607/92 |
| 5,079,262 A | 1/1992 | Kennedy et al. | 514/561 |

(List continued on next page.)

FOREIGN PATENT DOCUMENTS

| | | |
|---|---|---|
| DE | 2 707 920 | 8/1978 |
| DE | 2 823 615 | 12/1979 |

(List continued on next page.)

OTHER PUBLICATIONS

Documents Regarding Clinical Studies (D0001–D0133).
Mountford, "A UVA meter for monitoring the irradiance within a photochemotherapy unit", Physics in Medicine and Biology, vol. 28, No. 2, Feb. 1983, pp. 177–184.

(List continued on next page.)

*Primary Examiner*—Jeffrey R. Jastrzab
(74) *Attorney, Agent, or Firm*—Foley & Lardner

(57) ABSTRACT

An apparatus and method for photodynamic therapy or photodynamic diagnosis using an illuminator comprising a plurality of light sources generally conforming to a contoured surface and irradiating the contoured surface with substantially uniform intensity visible light. The light sources may comprise generally U-shaped fluorescent tubes that are driven by electronic ballasts. Adjustment of the ballast voltage controls the output power of the tubes. The tubes are supported by a sheet-metal or plastic housing and are covered by a polycarbonate shield which directs cooling airflow within the unit and prevents glass-patient contact in the event of tube breakage. An aluminum reflector located behind the tubes increases both the output irradiance and the uniformity of the output distribution. The spacing of the U-shaped tubes is varied to increase the output at the edges of the illuminator to make the output more uniform. Also, different portions of the tubes are cooled at different amounts, to improve uniformity. A light sensor monitors output from the U-shaped tubes to provide a signal for adjusting the output from the tubes.

26 Claims, 15 Drawing Sheets

U.S. PATENT DOCUMENTS

| | | | |
|---|---|---|---|
| 5,211,938 A | 5/1993 | Kennedy et al. | 424/7.1 |
| 5,219,998 A | 6/1993 | Levin et al. | 530/388.24 |
| 5,234,940 A | 8/1993 | Kennedy et al. | 514/410 |
| 5,258,453 A | 11/1993 | Kopecek et al. | 525/54.1 |
| 5,298,502 A | 3/1994 | Halling et al. | 514/185 |
| 5,344,434 A | 9/1994 | Talmore | 607/88 |
| 5,353,799 A | 10/1994 | Chance | 600/476 |
| 5,368,841 A | 11/1994 | Trauner et al. | 424/9 |
| 5,397,770 A | 3/1995 | Levin et al. | 514/2 |
| 5,422,093 A | 6/1995 | Kennedy et al. | 424/9.61 |
| 5,441,531 A | 8/1995 | Zarate et al. | 607/90 |
| 5,474,528 A | 12/1995 | Meserol | 604/20 |
| 5,489,279 A | 2/1996 | Meserol | 604/290 |
| 5,505,726 A | 4/1996 | Meserol | 606/9 |
| 5,556,612 A | 9/1996 | Anderson et al. | 424/59 |
| 5,565,685 A | 10/1996 | Czako et al. | 250/504 R |
| 5,626,631 A | 5/1997 | Eckhouse | 607/88 |
| 5,643,334 A * | 7/1997 | Eckhouse et al. | 607/88 |
| 5,645,578 A | 7/1997 | Daffer et al. | 607/91 |
| 5,707,401 A | 1/1998 | Talmore | 607/88 |
| 5,713,845 A | 2/1998 | Tankovich | 604/20 |
| 5,749,830 A | 5/1998 | Kaneko et al. | 600/160 |
| 5,755,751 A | 5/1998 | Eckhouse | 607/88 |
| 5,792,214 A * | 8/1998 | Larsson et al. | 362/130 |
| 5,829,448 A | 11/1998 | Fisher et al. | 128/898 |
| 5,832,931 A | 11/1998 | Wachter et al. | 128/898 |
| 5,833,612 A | 11/1998 | Eckhouse et al. | 600/476 |
| 5,836,999 A | 11/1998 | Eckhouse et al. | 607/88 |
| 5,845,640 A | 12/1998 | Lawandt | 128/664 |
| 5,861,020 A | 1/1999 | Schwarzmaier | 607/89 |
| 5,899,882 A | 5/1999 | Waksman et al. | 604/96 |
| 5,908,415 A | 6/1999 | Sinofsky | 606/7 |
| 5,919,217 A | 7/1999 | Hughes | 607/90 |
| 5,944,748 A | 8/1999 | Mager et al. | 607/88 |
| 5,947,959 A | 9/1999 | Sinofsky | 606/9 |
| 5,957,960 A | 9/1999 | Chen et al. | 607/88 |
| 5,961,543 A | 10/1999 | Waldmann | 607/88 |
| 5,971,918 A | 10/1999 | Zanger | 600/160 |
| 5,998,597 A | 12/1999 | Fisher et al. | 536/23.1 |
| 6,011,563 A | 1/2000 | Fournier et al. | 345/500 |
| 6,013,053 A | 1/2000 | Bower et al. | 604/96 |
| 6,045,575 A * | 4/2000 | Rosen et al. | 2/905 |
| 6,223,071 B1 * | 4/2001 | Lundahl et al. | 600/476 |
| 6,269,818 B1 * | 8/2001 | Lui et al. | 128/898 |
| 6,290,713 B1 * | 9/2001 | Russell | 607/88 |
| 6,350,275 B1 * | 2/2002 | Vreman et al. | 607/88 |
| 6,383,177 B1 * | 5/2002 | Balle-Petersen et al. | 606/9 |

FOREIGN PATENT DOCUMENTS

| | | |
|---|---|---|
| DE | 36 30 060 | 3/1988 |
| DE | 90 00 705.0 | 10/1990 |
| EP | 0 766 674 | 4/1997 |
| EP | 0 788 765 | 8/1997 |
| GB | 2 007 825 | 5/1979 |
| GB | 2 149 490 | 6/1985 |
| GB | 2 300 253 | 10/1998 |
| WO | 93/21842 | 11/1993 |

OTHER PUBLICATIONS

People, "Jessica Hahn an involuntary sex object, she made the most of it", p. 158, (1998).

Kennedy et al., "Photodynamic Therapy (PDT) and Photodiagnosis (PD) Using Endogenous Photosensitization Induced by 5–Aminolevulinic Acid (ALA): Mechanisms and Clinical Results", J. of Clinical Laser Medicine & Surgery, vol. 14, No. 5, 1996, pp. 289–304.

Annual Report Pursuant to Section 13 or 15(d) of the Securities Exchange Act of 1934, Form 10–K, DUSA Pharmaceuticals, Inc., pp. 4–5, (1997).

First Phase III, DUSA Pharmaceuticals, Inc. 1996 Annual Report, pp. 1–30, (1997).

Approval to Ship Investigational Devices, (Jan. 31, 1997).

DUSA Pharmaceuticals, Inc., Invoice, (Feb. 11, 1997).

Lumenentics, Confidential Summary Report, (Sep. 1996).

List of Study Start/Stop Dates, Patients and Centers, (Aug. 11, 1995 & Aug. 12, 1997).

Dr. Scott D. Glazer, Research Agreement, (Aug. 21, 1995).

Dr. Scott D. Glazer, Research Agreement, (Sep. 2, 1995).

Dr. Joseph F. Fowler, Jr., Research Agreement, (Jul. 15, 1996).

Clinical Study Agreement, (Apr. 2, 1997).

Research Agreement, (Nov. 15, 1996).

Linda L. Frattura, Approval Letter from Boston University Medical Center, (Apr. 30, 1996).

John M. Isidor, J.D., "Approval Letter from Schulman Associates Institutional Review Board, Inc.", (Apr. 10, 1997 & Dec. 2, 1996).

Dr. Scott D. Glazer, Informed Consent, (Aug. 10, 1995).

Dr. Scott D. Glazer, Informed Consent, (Aug. 23, 1995).

Dr. Joseph F. Fowler, Jr., Informed Consent, (Jul. 10, 1996).

Dr. Harold Farber, Informed Consent, (May 16, 1997).

Dr. Joseph F. Fowler, Jr; Dr. Robert H. Zax; Dr. Jeffrey P. Callen, Informed Consent, (May 7, 1997).

Dr. Joseph F. Fowler, Jr.; Lynn Fowler, R.N., Confidentiality Agreement between DUSA Pharmaceuticals, Inc. (Apr. 19, 1996).

Dr. Scott D. Glazer, Confidentiality Disclosure Agreement between DUSA Pharmaceuticals, Inc., (May 23, 1995).

Rob Danziger, Confidentiality Agreement between DUSA Pharmaceuticals, Inc., (Mar. 12, 1997).

* cited by examiner

ILLUMINATOR FOR PHOTODYNAMIC THERAPY AND DIAGNOSIS WHICH PRODUCES SUBSTANTIALLY UNIFORM INTENSITY VISIBLE LIGHT

This application is a divisional of application Ser. No. 09/070,772, filed May 1, 1998 now U.S. Pat. No. 6,223,071.

BACKGROUND OF THE INVENTION

1. Field of the Invention

The present invention is directed to photodynamic therapy using an illuminator that provides a uniform distribution of visible light. In particular, the present invention is directed to an apparatus and method for photodynamic treatment (PDT) or diagnosis (PD) of actinic keratosis of the scalp or facial areas of a patient. The present invention is also directed to an apparatus and method for PDT and PD of other indications (e.g., acne) and other areas of the patient (e.g., arms, legs, etc.).

As they are used here, the term "visible light" refers to radiant energy in the visible range of the electromagnetic radiation spectrum, and the term "light" refers to radiant energy including the ultraviolet (UV), infrared (IR) and visible ranges of the electromagnetic radiation spectrum.

2. Description of Related Art

Photodynamic therapy or photochemotherapy is currently being proposed to treat several types of ailments in or near the skin or other tissues, such as those in a body cavity. For example, PDT is being proposed to treat different types of skin cancer and pre-cancerous conditions. In PDT, a patient is administered a photoactivatable agent or precursor of a photoactivatable agent which accumulates in the tissue being diagnosed or treated. An area of the patient which includes the tissue being diagnosed or treated is then exposed to visible light. The visible light causes chemical and/or biological changes in the photoactivatable agent which in turn selectively locate, destroy or alter the target tissue while at the same time causing only mild and reversible damage to other tissues in the treatment area.

General background information on PDT using 5-aminolevulinic acid ("ALA") as the precursor of a photoactivatable agent can be found in U.S. Pat. No. 5,079,262, entitled "Method of Detection and Treatment of Malignant and Non-Malignant Lesions Utilizing 5-Aminolevulinic Acid," issued to James C. Kennedy et al. on Jan. 7, 1992, and U.S. Pat. No. 5,211,938, entitled "Method of Detection of Malignant and Non-Malignant Lesions by Photochemotherapy of Protoporphyrin IX Precursors," issued to James C. Kennedy et al. on May 18, 1993. The contents of these patents are incorporated herein by reference. The publication of James C. Kennedy et al. in the Journal of Clinical Laser Medicine and Surgery on Nov. 5, 1996, entitled "Photodynamic Therapy (PDT) and Photodiagnosis (PD) Using Endogenous Photosensitization Induced by 5-Aminolevulinic Acid (ALA): Mechanisms and Clinical Results," is also incorporated herein by reference. The "First Phase III" 1996 Annual Report by DUSA Pharmaceuticals, Inc. (Tarrytown, N.Y.) contains pictures and examples of use of the invention, and is also incorporated herein by reference.

As they are used here, the terms ALA or 5-aminolevulinic acid refer to ALA itself, precursors thereof and pharmaceutically acceptable salts of the same.

Most conventional, non-laser light sources are comprised of just three basic functional blocks: an emission source to generate photons (e.g., a light bulb); coupling elements to direct, filter or otherwise conduct the emitted light so that it arrives at the intended target in a usable form; and a control system to start and stop the production of light when necessary. The common office fluorescent lighting fixture is a good example of such a system. In these fixtures, white visible light is produced by a controlled mercury arc discharge which excites inorganic phosphor materials inside a glass tube. Energy transfer from the arc causes visible white light emission from the tube. The emitted visible light is directed toward the work space by reflectors in the lamp housing; the distribution of visible light to the target is often further increased by using a diffusing system. In the typical office setting, visible light production is controlled by a simple snap switch which interrupts the flow of power to the lamp.

For therapeutic reasons it is desirable to have a power output which is uniform in intensity and color. In particular, it is highly desirable to have an illuminator with a spectral output that overlaps to a large extent with the optical activation spectrum of the target photosensitizer. According to one preferred embodiment of the present invention, blue light having wavelengths exceeding 400 nm (nanometers) is particularly advantageous for certain diagnostic purposes and treatments, especially when ALA is the photoactivatable agent used for PD and PDT of actinic keratosis. However, visible light in other ranges of the spectrum, particularly in the green and red ranges between 400 and 700 nm, may also be used.

Conventional illuminators do not produce visible light that is sufficiently uniform in intensity over a contoured surface.

SUMMARY OF THE INVENTION

It is an object of the present invention, therefore, to provide an improved illuminator for PDT and/or PD.

Another object of the invention is to provide an illuminator for PDT that produces visible light of consistent uniformity in terms of both spectral characteristics and intensity over a diversely contoured surface. As it is used here, the term contoured surface refers to a non-planar surface.

Yet another object of the invention is to provide an illuminator for PDT or PD which produces visible light almost entirely in a selected wavelength range.

A further object of the present invention is to provide an illuminator for irradiating the face or scalp of a patient.

Yet a further object of the present invention is to provide a cooling system for improving the irradiance uniformity of an illuminator.

An additional object of the present invention is to provide an illuminator comprising a finite emitter that approximates the uniform output of an infinite plane emitter by varying the spacing of individual light sources within the illuminator.

Yet an additional object of the present invention is to provide a monitoring system for an illuminator comprising a single visible light sensor monitoring the visible light output of a plurality of light sources and outputting a signal to adjust the visible light output from the plurality light sources.

In accomplishing the foregoing objects, there has been provided according to the present invention an illuminator for PDT or PD of a contoured surface. The illuminator comprises a plurality of light sources generally conforming to the contoured surface and irradiating the contoured surface with substantially uniform intensity visible light, and a housing supporting the plurality of light sources with respect to the contoured surface.

In accomplishing the foregoing objects, there is also provided according to the present invention a method of PDT or PD of a contoured surface. The method comprises topically applying 5-aminolevulinic acid to the contoured surface, and irradiating the contoured surface with substantially uniform intensity visible light from a plurality of light sources generally conforming to the contoured surface.

In accomplishing the foregoing objects, there is also provided according to the present invention a cooling system for an illuminator including an elongated light source having a generally arcuate segment connected to a generally straight segment. The cooling system comprises a plenum enclosing the light source; an intake vent to the plenum receiving ambient air, the intake vent being positioned proximate a free end of the generally straight segment; and an exhaust vent from the plenum discharging heated ambient air, the exhaust vent being positioned proximate a connection between the generally arcuate and straight segments. The generally straight segment and a connection between the generally arcuate and straight segments receives greater cooling relative to the generally arcuate segment.

In accomplishing the foregoing objects, there is also provided according to the present invention a method of providing substantially uniform intensity light from an elongated light source having a generally arcuate segment connected to a generally straight segment. The method comprises providing greater cooling to the generally straight segment relative to the generally arcuate segment.

In accomplishing the foregoing objects, there is also provided according to the present invention an illuminator for emulating an infinite plane emitter. The illuminator comprises an emitting area having a perimeter, and a plurality of light sources being generally parallel to one another, said plurality of light sources being adapted for irradiating substantially uniform intensity light from said emitting area. Lateral spacing between adjacent ones of said plurality of light sources varies with respect to said perimeter.

In accomplishing the foregoing objects, there is also provided according to the present invention a monitoring system for an illuminator irradiating a surface. The monitoring system comprises a plurality of adjustable light sources adapted for irradiating the surface with substantially uniform intensity light; a light sensor being supported with respect to the plurality of light sources; a partition interposed between the light sensor and the plurality of light sources; a first aperture in the partition adapted for admitting light from a first one of the plurality of light sources to the light sensor, the first aperture being spaced from the light sensor a first distance and having a first cross-sectional area; and a second aperture in the partition adapted for admitting light from a second one of the plurality of light sources to the light sensor, the second aperture being spaced from the light sensor a second distance and having a second cross-sectional area. A ratio of the first and second cross-sectional areas is proportional to inverse squares of the first and second distances; and the light sensor is adapted for monitoring light output from the first and second ones of the plurality of light sources and outputting a signal to adjust light output from the plurality of light sources so as to provide the substantially uniform intensity light irradiating the surface.

In accomplishing the foregoing objects, there is also provided according to the present invention light for photodynamically diagnosing or treating a contoured surface, the light coming from a plurality of sources generally conforming to the contoured surface and irradiating the contoured surface with uniform intensity.

The present invention relies on similar fundamentals to that of the office fluorescent lighting system described above. According to an embodiment of the present invention: visible light is produced by contour surface conforming fluorescent tubes and their associated control electronics; visible light output from these tubes is directed toward the diagnosis or treatment area by the contour surface conforming shape of the tubes and other elements such as a reflector; and activation of the fluorescent tubes and visible light exposure on the contoured surface is controlled by the electronic circuitry.

The present invention differs from conventional light sources because of the biological requirements imposed on a PDT light source. A much higher degree of precision and integration is required for the components of the present invention. Output spectrum, irradiance, and irradiance uniformity all must be controlled to assure that the properties of the device are suitable to deliver light to the target lesions and drive the photodynamic reaction. To achieve this, each functional block within the present invention comprises carefully selected and engineered components. The principles of operation of each are described in detail below.

The inverse square law of optics states that the intensity of light from a point source received by an object is inversely proportional to the square of the distance from the source. Because of this behavior, distance from the source is an important variable in all optical systems. Thus, in order to achieve uniform facial or scalp irradiation, variations in output irradiance with distance must be minimized. A flat emitting surface would not deliver a uniform light dose to all contours of the face simultaneously because the non-planar facial and scalp surfaces could not be placed at a constant distance from the emitting surface. To ameliorate this problem, the present invention uses a U-shaped emitting surface that more closely follows the contours of the human face and scalp, and minimizes lamp to target distance variations which in turn minimizes irradiance variations at the target.

Since the output of tubular light sources may vary with temperature, temperature distribution also plays a key role in irradiance uniformity. Further, since the tube output may vary over its length, modulation of the temperature distribution may be used to control irradiance uniformity of the illuminator.

Additional objects, features and advantages of the invention will be set forth in the description which follows, and in part will be clear from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and, together with the general description given above and the detailed description of the preferred embodiments given below, serve to explain the principles of the invention.

DETAILED DESCRIPTION OF PREFERRED EMBODIMENTS

Overview

Figure 1:
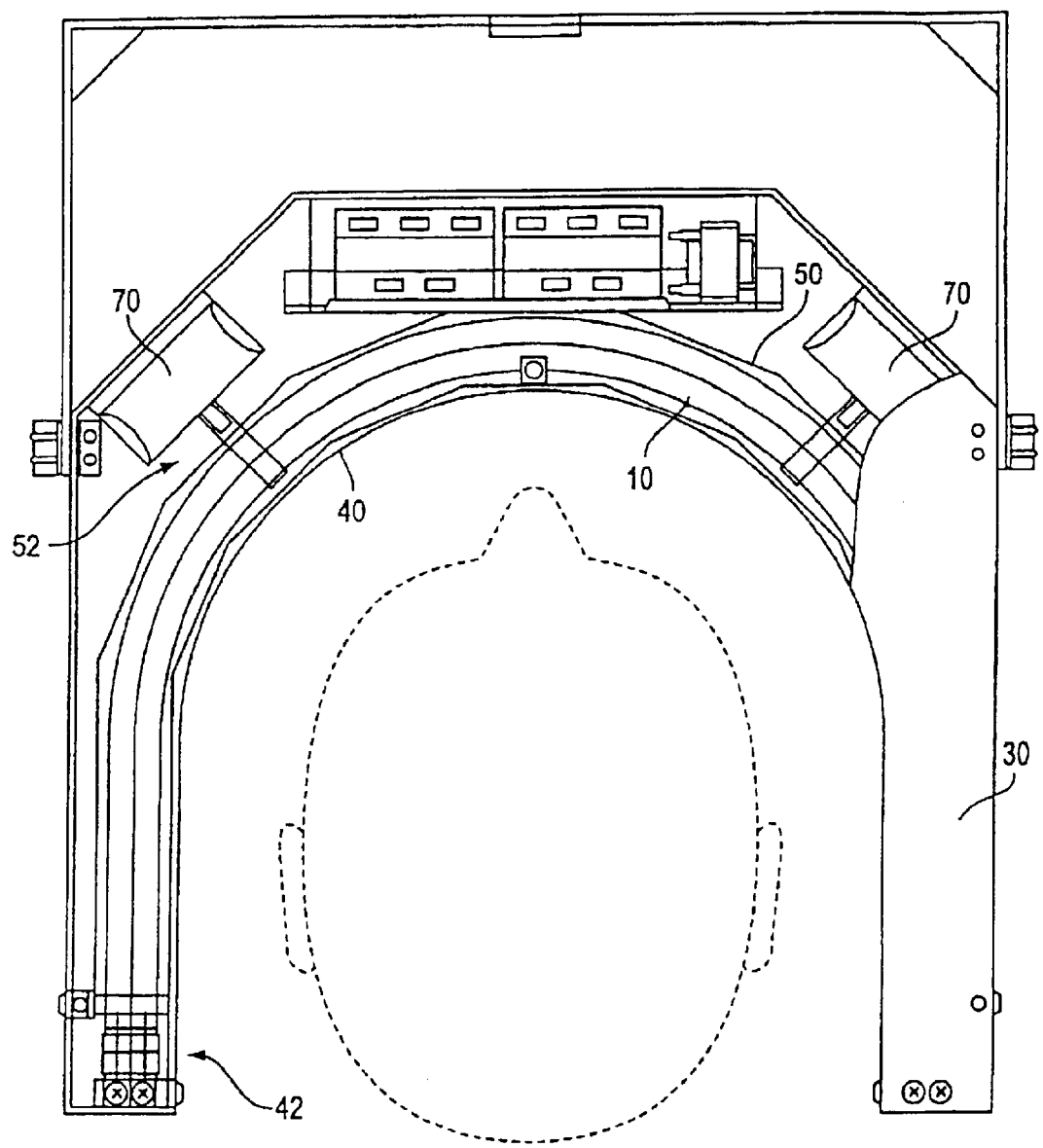
FIG. 1 is a partial cross-section, front elevation view of an illuminator according to the present invention.

According to one preferred embodiment illustrated in FIGS. 1–8, seven U-shaped fluorescent tubes 10(1)–10(7) are driven by three electronic ballasts 20. Adjusting the ballast voltage controls the output power of the tubes. The tubes 10(1)–10(7) are supported by a housing 30 and are covered by a polycarbonate shield 40 which directs cooling airflow within the unit and prevents glass-patient contact in the event of tube breakage. An aluminum reflector 50 located behind the tubes increases both the output irradiance and the uniformity of the output distribution. The overall dimensions of the unit are approximately 38 cm H×45 cm W×44.5 cm D. FIG. 1 shows the position of the patient's head and nose.

Exemplary Light Sources

According to a preferred embodiment of the present invention, seven 36" U-shaped F34T8 Ultra Blue fluorescent tubes 10(1)–10(7) provide a maximum visible light-emitting area 36 cm high by 46 cm wide (approximately 2850 cm$^2$), with a minimum therapeutically active area 30 cm high by 46 cm wide (approximately 1350 cm$^2$). As shown in FIG. 1, the tubes have a generally arcuate central region 10A and arms 10B extending from respective ends of the central region.

Fluorescent tubes are a type of gas discharge lamp. They utilize an electric discharge through a low pressure gas to create a plasma which interacts with a fluorescing phosphor to convert electrical energy into light. A typical fluorescent tube consists of a sealed glass tube with electrodes, or cathodes, at both ends. The tube is internally coated with a uniform luminescent inorganic crystalline phosphor. The tube is filled with a low pressure inert gas, usually argon, to which a small amount of liquid mercury is added prior to sealing. The low internal pressure causes some of the liquid mercury to evaporate resulting in an argon/mercury atmosphere within the tube. Application of a sufficiently high voltage potential across the cathodes causes the emission of electrons from the cathode, which diffuse along the length of the tube and ionize the argon/mercury vapor. Once ionized, the gas mixture within the tube becomes conductive which permits an electrical current to flow and continue to excite the mercury atoms. The magnitude of the tube current controls the number of excited atoms and hence the light output from the tube. As the excited mercury atoms return to a lower energy state, they emit ultraviolet (UV) radiation. This UV radiation is absorbed by the phosphor on the tube wall causing the phosphor to fluoresce, efficiently converting the energy of the principle resonant line of mercury to a longer wavelength. The chemistry of the phosphor material determines the characteristic spectral emission of the light output from the lamp. This can be utilized to tune the wavelength output of the light source to suit the requirements of the application, as is the case in the present invention.

Figure 2:
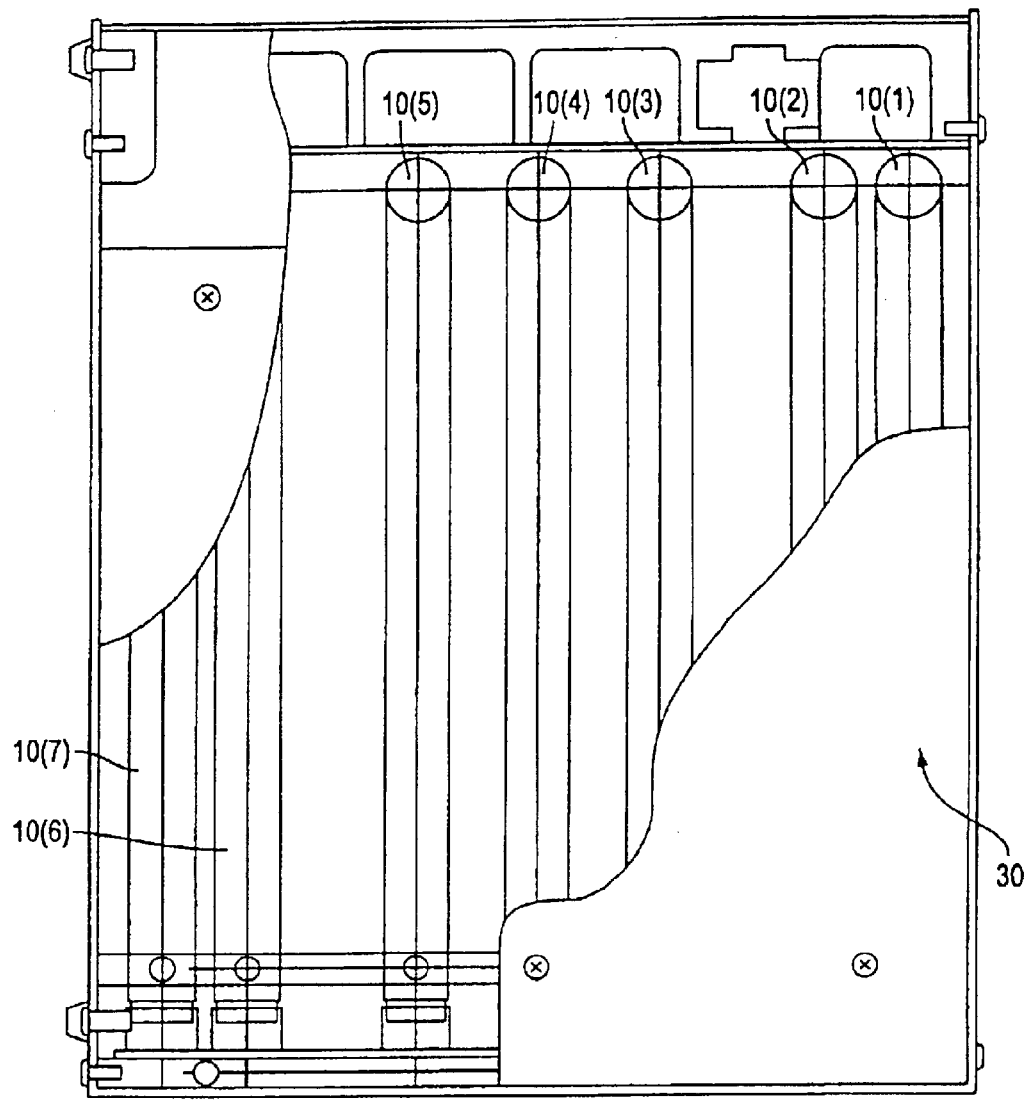
FIG. 2 is a partial cross-section, side elevation view of the illuminator shown in FIG. 1.
Figure 3:
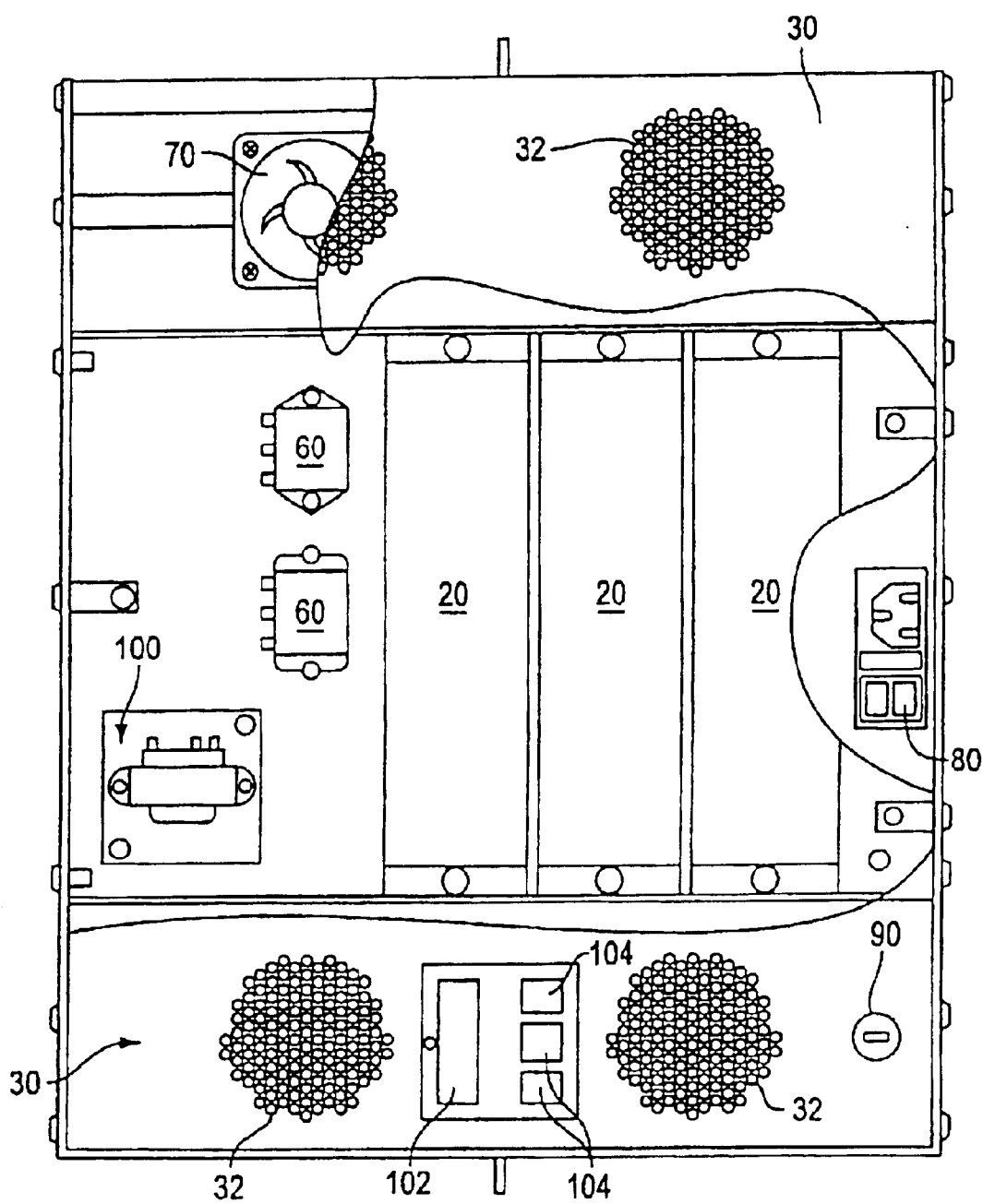
FIG. 3 is a partial cross-section, plan view of the illuminator shown in FIG. 1.
Figure 4A:
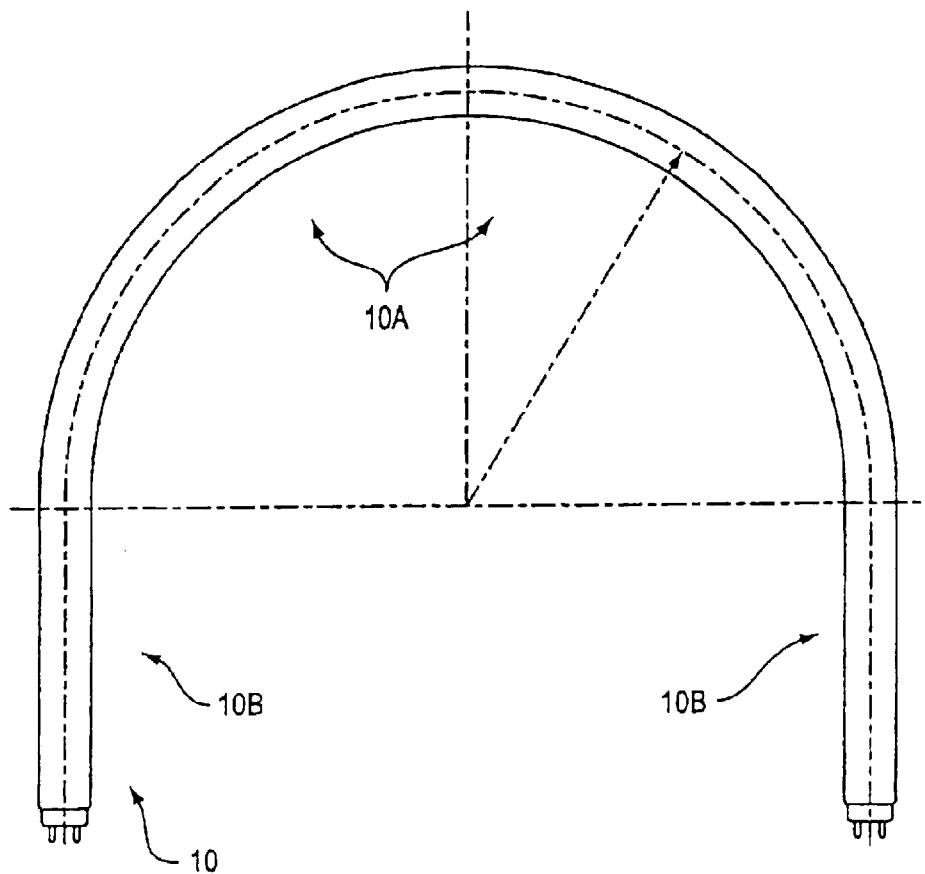
FIG. 4 is a detail view of the fluorescent tube light source shown in FIG. 1.
Figure 4B:
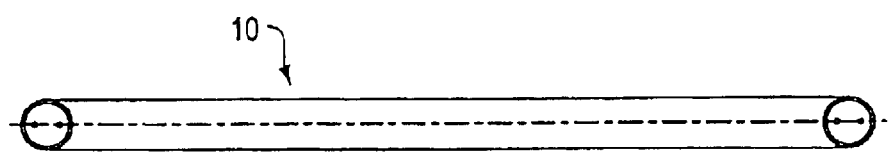
Figure 5A:
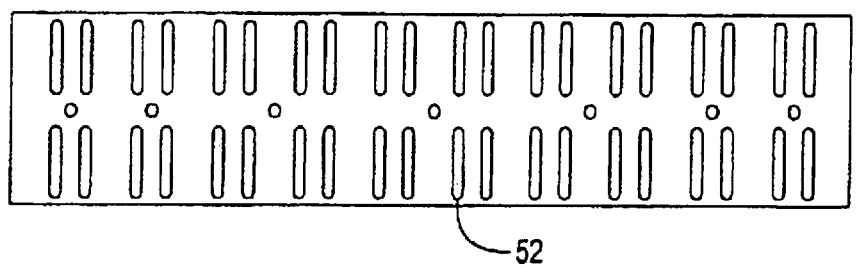
FIG. 5 is a detail view of the reflector shown in FIG. 1.
Figure 5B:
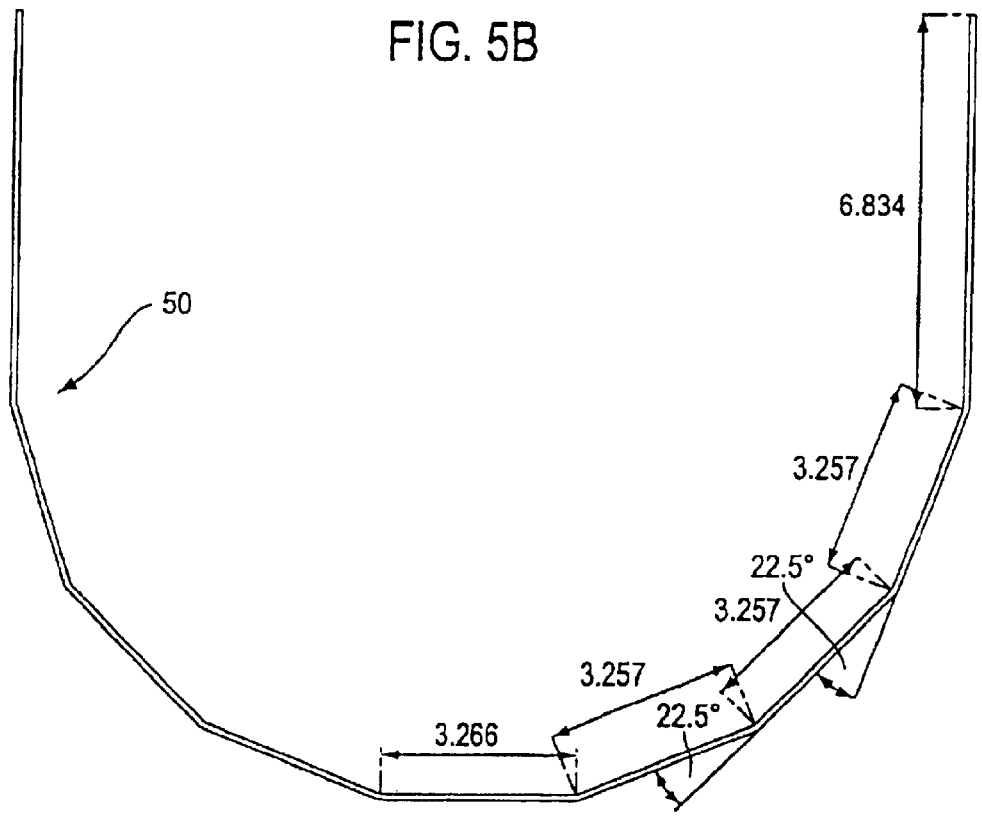
Figure 6:
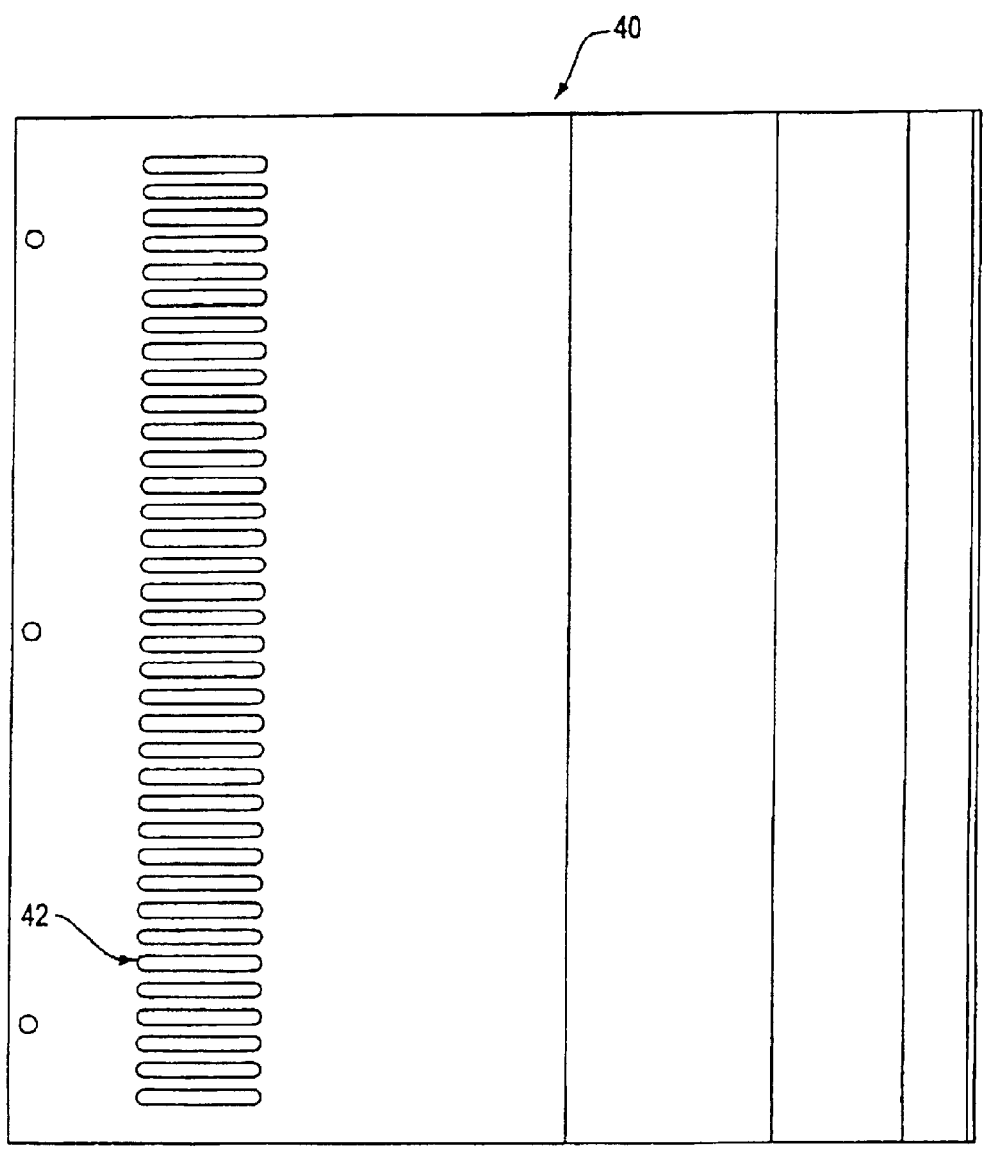
FIG. 6 is a detail view of the shield shown in FIG. 1.
Figure 7:
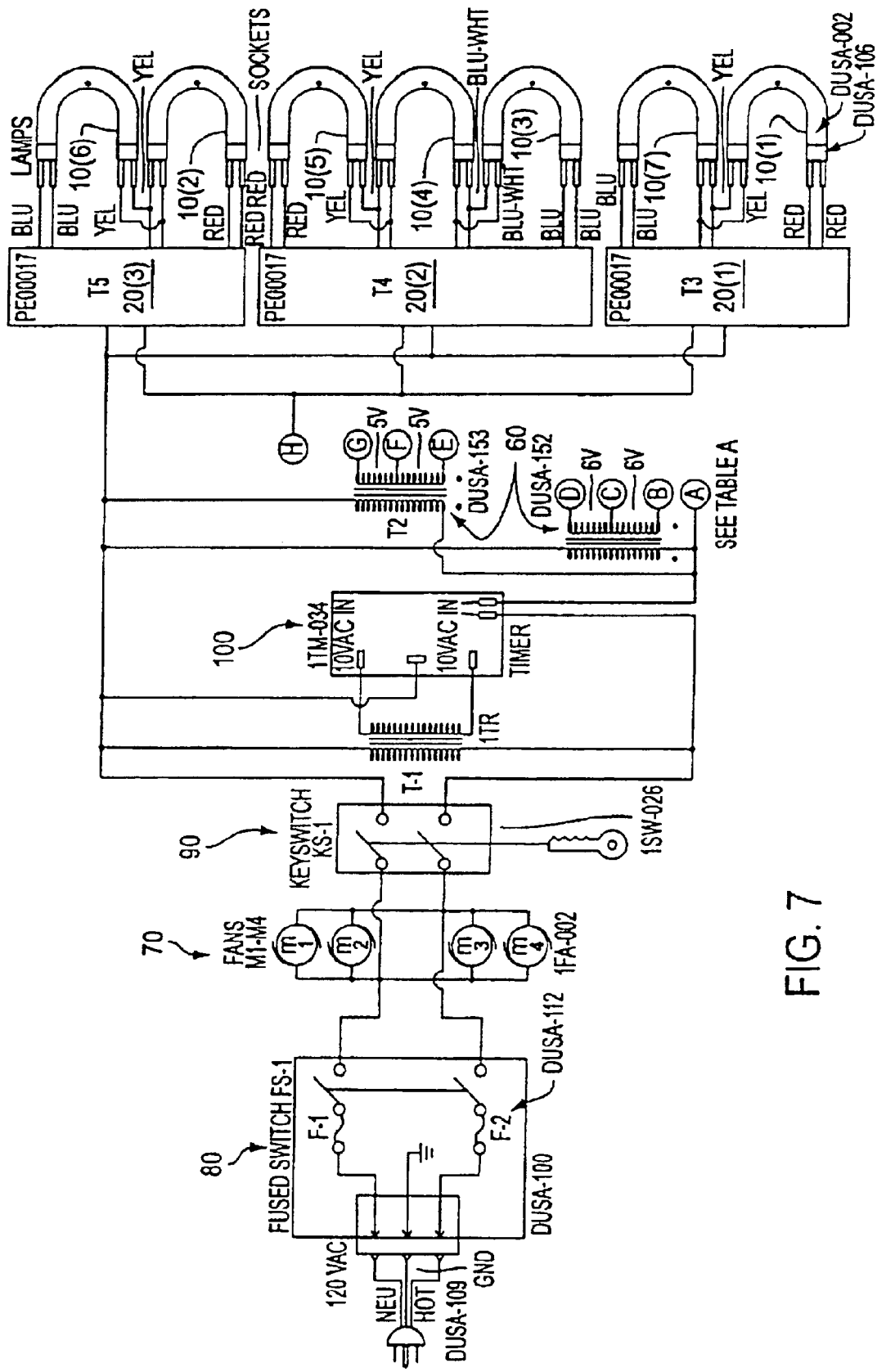
FIG. 7 is a schematic illustration of a wiring circuit for the illuminator shown in FIG. 1.
Figure 8:
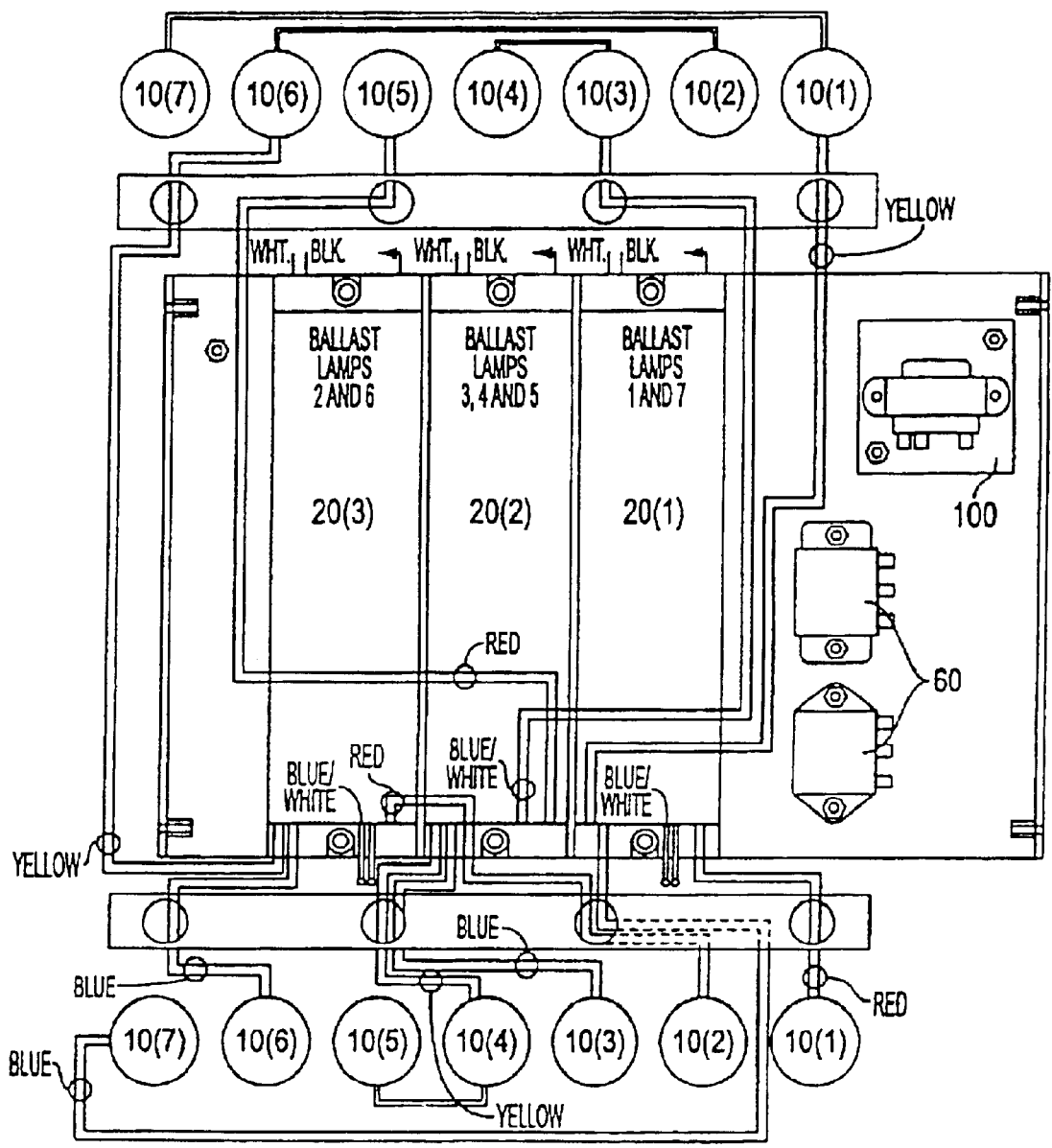
FIG. 8 is a schematic illustration of a ballast wiring circuit for the illuminator shown in FIG. 1.

The output from a fluorescent tube is not inherently uniform. The output measured in the immediate vicinity of the cathode is typically much lower than the output over the rest of the tube. This occurs because ionized gas in the area near the cathode does not emit as much UV to excite the phosphor. This area of reduced emission is known as the Faraday dark space. To avoid uniformity problems, one embodiment of the present invention utilizes a plurality of U-shaped tubes 10(1)–10(7). This arrangement allows the cathodes and their low output area to be located outside the active emitting area (effectively behind the patient's ears). Only the more uniform center portion of the tube output is used for patient treatment. Another advantage of the arrangement is that uniformity can also be adjusted by varying the lateral spacing of the tubes (relative horizontal spacing as shown in FIG. 2). This is important since it is necessary to compensate for the fact that the output from a flat plane emitting light source drops near the edges. Varying the lateral spacing of the tubes creates the same effect as folding the edges of a larger illuminator in on itself, thus emulating an infinite plane emitter with a compact unit.

The U-shape minimizes the variations in distance between the emitter and the target, providing a uniform visible light distribution to the face or scalp of the patient; the tube dimensions were chosen based on the average dimensions of the adult human head. The mounting of the tubes minimizes the impact of the non-emitting area at their ends. This allows the present invention to be more compact and permits easier centering of the patient's head within the visible light sources. Moreover, the "U" shape provides the desired irradiance and irradiance uniformity for scalp and facial irradiation, and thus ensures that the proper visible light dosage is applied to all target areas during PDT.

The number of tubes used and the spacing between them were chosen to achieve desired uniformity and power output specifications. Optimum output distribution has been found to occur when seven tubes 10(1)–10(7) are placed in the chassis in a symmetric pattern with respect to opposite edges of the unit with the following approximate lateral spacing: 7 cm between the center tube 10(4) and each of the two tubes 10(3),10(5) adjacent to the center tube 10(4); 5 cm between the tubes 10(3),10(2) and 10(5),10(6), i.e., the next pairs of tubes out from the center; and 3.5 cm between tubes 10(2),10(1) and 10(6),10(7), i.e., the outermost pairs of tubes at the sides of the unit. The outermost tubes 10(1),10(7) are approximately 2.5 cm from the edges of the housing. The present invention provides a highly uniform output irradiance without the use of an additional diffusing element. However, it is also envisioned that a diffusing element could also be incorporated into the shield 40.

Figure 10:
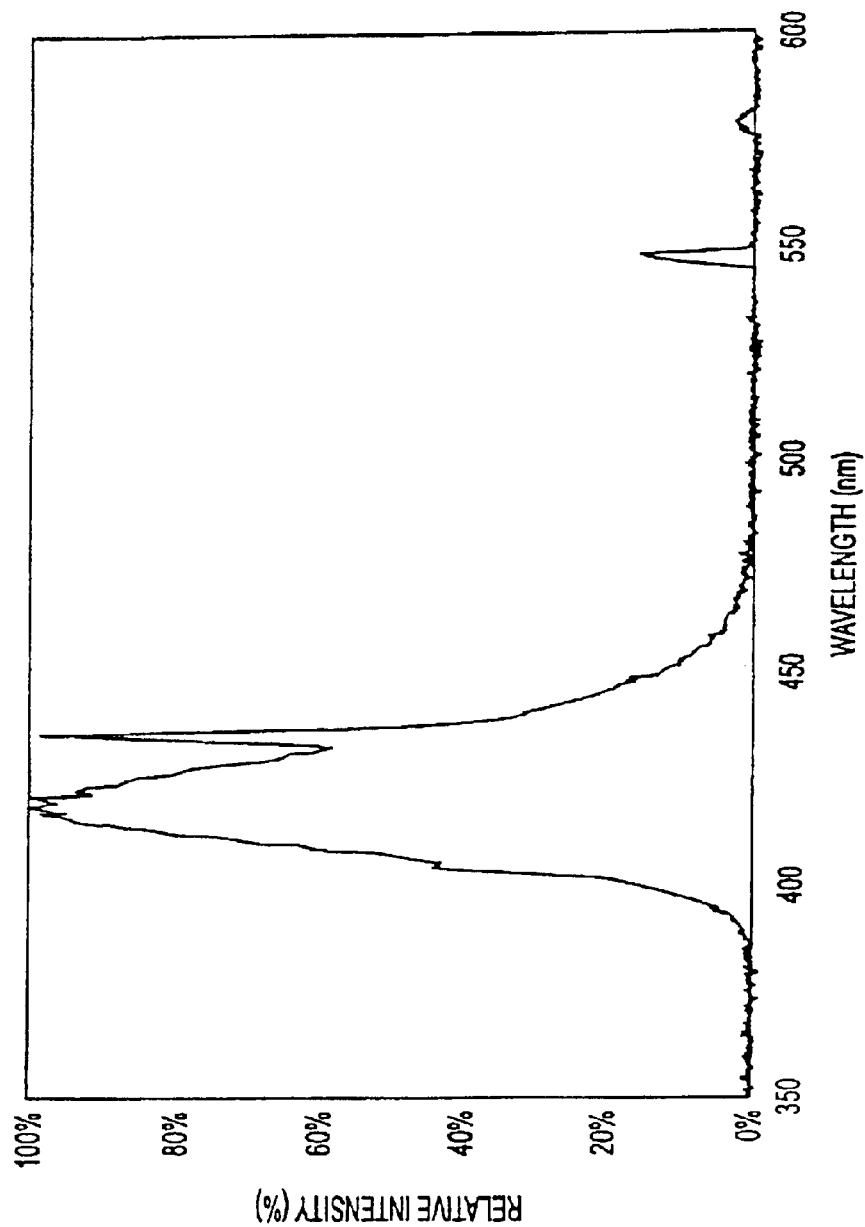
FIG. 10 is an illustration of a typical fluorescence emission spectrum of the fluorescent tube light source shown in FIG. 4.

The fluorescent tubes according to preferred embodiments of the present invention utilize a commercially available phosphor—$Sr_2P_2O_7$:Eu—that is used in the diazo blue-printing process. When this phosphor absorbs the UV radiation emitted from the mercury it produces an emission spectrum of blue light with a bandwidth having a range of 30 nm at a peak wavelength of 417 nm (nominal). A typical fluorescence emission spectrum of the tubes according to the present invention is shown in FIG. 10. According to a preferred embodiment of the present invention, the spectral output is selected to match the absorption spectrum of protoporphyrin IX, the photosensitizing species thought to be formed from ALA in target tissue. Other visible spectral outputs may be provided when utilizing a different phosphor within the tubes. Other visible spectral outputs may also be provided when utilizing other light source technologies.

Electrical Features

Achieving satisfactory performance from a fluorescent tube requires the application of a voltage to the tube cathodes to initiate tube conduction and subsequently control the tube current. Fluorescent tubes, being gas discharge devices, are particularly sensitive to the electrical voltages and currents used to drive them. Higher tube currents will increase the electron yield causing the output irradiance to increase. But higher currents result in higher cathode temperatures, potentially increasing the erosion of the cathode emitting material and contamination of the tube atmosphere by material removed from the cathodes; this ultimately results in decreased tube life. Tube currents that are too low can result in low tube wall temperatures that may cause condensation of the mercury vapor, adversely affecting the uniformity of the lamp output. Furthermore, for most tube designs it is necessary to heat the cathodes to achieve proper tube starting. Control of the voltage and/or tube current characteristics, as well as heating of the cathodes is accomplished with external electronic circuitry which is usually engineered and packaged into a single device commonly referred to as a "ballast". There are many such ballast designs possible; they range from simple electromagnetic inductors to sophisticated electronic circuits that optimize and control many aspects of tube operation.

According to a preferred embodiment of the present invention, each ballast 20 comprises three main functional sections: an input filtering circuit, a power oscillator circuit, and a high frequency output transformer.

The input filter circuit rectifies the 120 VAC line voltage into an internal DC voltage that can be utilized by the power oscillator. The filter also prevents disturbances on the AC line from adversely affecting the operation of the ballast and prevents oscillator switching transients from feeding back into the AC line. Lastly, this circuit provides power factor correction so that the peak AC line current drawn by the ballasts is lower than that for a simple rectifier. It is also possible to operate preferred embodiments of the present invention using DC input voltage.

The power oscillator provides the mechanism for electrical energy transfer in each ballast unit 20; it consists of a pair of switching transistors coupled to a resonant circuit which includes the output transformer. A small signal from the output transformer is fed back to the input of the switching transistors causing them to oscillate when the DC voltage is applied. Energy from this oscillation is coupled through the transformer to the tubes. For this ballast design, the magnitude of the oscillation is proportional to the DC voltage which in turn is proportional to the AC line voltage. Because the transformer is also connected to the tube cathodes, the magnitude of the tube current is proportional to the AC line voltage. This is known as a non-constant wattage design and it was chosen to allow adjustment of the output irradiance of the present invention.

The high frequency transformer couples energy to the tube, as well as performing several other important functions. It provides electrical transformation of voltage levels and a current limiting impedance in order to supply the correct voltage and current to the tubes to ensure proper and safe operation. It also provides feedback to the oscillator to help stabilize its operation and to supply a mechanism to generate an initial high voltage starting pulse.

Additional windings of the transformer also provide a current to heat the tube cathodes. This lowers the starting voltage requirements and reduces damage to the cathodes from the initial starting current surge.

Because of manufacturing variations in the production of the tubes, the output irradiance must be adjusted to meet the requirements for the specific PDT indication. Furthermore, the output must be adjusted as the tubes age to compensate for degradation within the tubes themselves. In a preferred embodiment of the present invention, ballasts 20 are non-constant wattage ballasts, thus allowing the tube output to be adjusted by changing the input voltage to the ballasts. According to a preferred embodiment of the present invention, a 40% variation is possible through the use of two buck/boost auto-transformers 60 on the AC line.

The ballast voltage may be adjusted manually or automatically. According to embodiments of the present invention having manual voltage adjustment, the appropriate ballast voltage is set by a technician manually selecting the taps on two buck/boost auto transformers 60. Since variations in input AC line voltage affect the ballast voltage, external voltage stabilization may be used to improve the stability of the output. Another preferred embodiment of the present invention has automatic voltage adjustment including an "active" system of microcontroller-activated electronic switches to eliminate the need for external voltage stabilization and the need for technician-adjustment of the ballast voltage as the tube output decreases with use. The microcontroller accepts input signals from optical and voltage sensors and then activates the appropriate electronic switch to maintain output irradiance within specified parameters. The active switching system is also able to correct for changes in power output due to line voltage and temperature variation during treatment; thus external line voltage stabilization is not required in a preferred embodiment of the present invention having the active switching system. Automatic voltage adjustment according to a preferred embodiment of the present invention is be described more fully below.

According to one preferred embodiment of the present invention, three rapid-start electronic ballasts 20 are utilized to drive seven fluorescent tubes 10(1)–10(7). Two of the ballasts 20(1) and 20(3) drive two tubes 10(1),10(7) and 10(2),10(6), respectively, and one ballast 20(2) drives three tubes 10(3)–10(5). These ballasts convert 120 VAC line voltage available from a standard wall outlet into a high frequency (~25 kHz) sinusoidal current suitable for driving the fluorescent tubes. High frequency operation is desirable to reduce the optical output ripple which is present in all fluorescent tubes and to increase the overall output. Output ripple is a small variation in the tube output related to the sinusoidal alternating tube current used to sustain the plasma arc.

Visible Light Transmission Features

In order to utilize the visible light emitted from the back of the tubes, and to increase the uniformity of the output distribution, a reflector 50 is positioned approximately 10 mm from the rear surface of the tubes. The reflector 50 is made of polished aluminum sheet which is bent to approximately conform to the configuration of the tubes.

The emitting area of the present invention is covered with a low UV transmission plastic shield 40. In a preferred embodiment of the present invention, plastic shield 40 is made from polycarbonate. When fluorescent tube technology is utilized, there is a small quantity of UV emission present in the output. Polycarbonate has very low transmission in the UV region of the spectrum and it effectively filters out any residual UV emission from the visible light output of the unit. The shield 40 also protects the patient from injury in the event of tube breakage.

Cooling Features

Since cathode and tube wall temperatures strongly affect the output distribution, a cooling system is provided to ensure proper bulb operation. According to an embodiment of the present invention, the cooling system comprises vents in the polycarbonate shield 40, the reflector 50 and the housing 30, as well as fans 70 to displace cooling air.

Ambient air enters the present invention through intake vents 42 in the polycarbonate shield 40. The space between the shield 40 and the reflector 50 creates a first zone (i.e., a plenum) in which the ambient air passes over the tubes 10(1)–10(7). The ambient air is heated by the tubes, and is transferred from the first zone to a second zone between the reflector 50 and the housing 30 through vents in the reflector 52. The reflector vents 52 are located at ±45° to provide the proper temperature distribution at the tube walls. Heated air is exhausted by four fans 70 through exhaust vents 32 in the housing 30.

According to a preferred embodiment of the present invention, a plurality of intake vents 42 (thirty-six are illustrated) in the polycarbonate shield 40 are evenly spaced along each edge directly over the cathode area of the tubes. The vents 52 in the reflector 50 are pairs of slots machined in columns from its top to its bottom; the reflector vents 52 are directly in front of the fans 70 which are located at ±45° from the center of the unit.

The straight section of the tube between the cathode area and curved section of the "U" tubes produces slightly more output than the center portion of the curved section. This has been attributed to differences in the phosphor coating thickness caused by the bending process. To further increase irradiance uniformity, the reflector vents 52 are located in the reflector 50 so that cooling air flows primarily over the straight section and the end portions of the curved section. Less cooling air flows over the middle of the tubes between the sets of reflector vents 52, causing the tube wall temperature to be higher in this region. Since the output irradiance for this tube increases (to a point) with tube wall temperature, the hotter central region of the tube produces higher output irradiances than the rest of the tube and compensates for the lower emission efficiency of the central region.

Basic Control Features

The user controls according an embodiment of the present invention include a main power switch 80 located on the back of the housing 30, and an on/off key switch 90 and a timer 100, located on a side of the housing 30. The timer 100 includes an exposure time indicator 102 that displays the remaining treatment time.

The main power switch 80 is part of a fused power entry module consisting of a two position rocker switch and an International Electrotechnical Commission (IEC) standard power cord connector. Pushing the rocker switch to the "1" position supplies power to the system. The fans 70 will operate but the tubes 10(1)–10(7) will not light until the key switch 90 is turned on and the timer 100 is set and activated. When the main power switch 80 is in the "0" position all electrical components within the present invention are disconnected from the AC line. The fused power entry module provides over-current protection to the present invention and current limiting in the event of a power surge; the main power switch 80 will not apply power to the unit if either fuse in this module has blown.

The key switch 90 provides a means by which use of the present invention can be restricted to authorized personnel. According to an embodiment of the present invention, operation of the timer 100 and tubes 10(1)–10(7) requires inserting the key and rotating it clockwise ¼ turn to the "ON" position. This activates the timer 100 so that the prescribed exposure time can be entered.

According to an embodiment of the present invention, the system timer 100 directly controls the operation of the fluorescent tubes 10(1)–10(7). It contains three adjustment/control buttons 104: one start/stop and two time select buttons, as well as the exposure time indicator 102. The timer 100 is used to set the required exposure time and to initiate visible light exposure. It automatically turns off the present invention tubes after the set exposure time has elapsed.

The two time select buttons 104 are preferably membrane switches that enable the user to set the exposure time. Depressing the button 104 with the "up" arrow increases time and depressing the button 104 with the "down" arrow decreases time. When first depressed, these buttons will change the display reading slowly. If they remain depressed, the display will begin to scroll more rapidly. Small adjustments to the displayed time can be made by quickly depressing and releasing these buttons. In this manner, the prescribed treatment time may set by the user.

The start/stop button 104 is a membrane switch that controls the tube operation; it toggles between the running and stopped states of the tubes and timer. After the exposure time has been set, depressing this button 104 activates the tubes and initiates the timer countdown sequence. Depressing it a second time turns off the tubes and stops the timer, thus providing a means for interrupting treatment if required. If the start/stop button 104 is not pressed a second time, the timer automatically turns off the tubes at the completion of the timer countdown. Treatment may also be terminated, if necessary, by rotating the key to the OFF position or by pushing the main power switch 80 to the "0" position.

The exposure time indicator 102 on the timer 100 is preferably a four digit LED display which reads in minutes and seconds. Prior to pushing the start/stop button 104 to begin light exposure, the display 102 indicates the exposure time that has been set. When the start/stop button 104 is depressed to initiate treatment, the exposure time indicator 102 will count down and display the amount of exposure time remaining. The tubes will automatically turn off when the display reads "00:00".

Power is supplied via a three conductor hospital grade electrical cord. The power requirements according to an embodiment of the present invention are 120 VAC, 2.5 amps, 60 Hz AC line voltage input that is stabilized using an external commercial voltage regulator (e.g., a SOLA MCR1000 constant voltage transformer).

Automatic Control Features

According to a preferred embodiment of the present invention, the need for technician-adjustment of the ballast voltage as the tube output decreases with use is eliminated by providing automatic self-adjustment of the ballast voltage. This has been accomplished by replacing the manual tap selection jumpers with an "active" system of microcontroller-activated electronic switches (FIGS. 9 and 9A–9D). The microcontroller accepts input signals from optical and voltage sensors and then activates the appropriate electronic switch to maintain output irradiance within specified parameters. The active switching system is able to correct for changes in power output due to line voltage and temperature variation during treatment; thus external line voltage stabilization is not required according to preferred embodiments of the present invention having automatic adjustment of the ballast voltage. All other components of the automatic ballast voltage adjusting embodiments of the present invention, including the tubes 10(1)–10(7), ballasts 20, reflector 50, and polycarbonate shield 40, are the same as for the manually adjusted embodiments.

Figure 11:
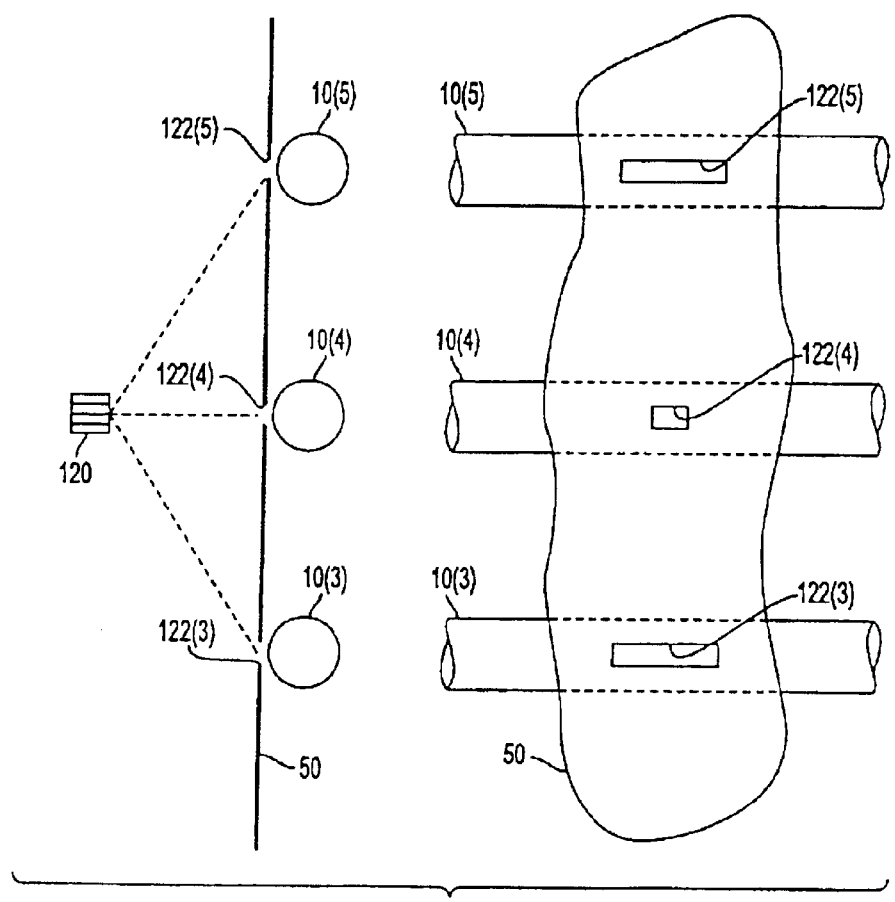
FIG. 11 is a depiction of a monitoring system according to the present invention.

According to a preferred embodiment of the present invention, an electronic control system 110 consists of six functional blocks. A microcontroller 200 is the central processing unit; it contains firmware which reads the system sensors, determines the system status, controls the ballast voltage (and tube output), and provides user information by way of a system status LED 112 (the firmware is described in detail below). To achieve output irradiance in the specified range, the microcontroller 200 monitors the tube output via a visible light sensor 120 which is located behind the tube reflector 50. Referring to FIG. 11, diffuse visible light is provided to the visible light sensor 120 by machining slots 122(3)–122(5) behind each of the center three tubes 10(3) –10(5) on the reflector panel 50 just left of the center. A voltage detection circuit 210 tells the microcontroller 200 when the timer 100 has initiated its countdown sequence and also when the maximum allowable ballast voltage has been reached. Using input from these sensors, the microcontroller 200 compares the current system status with the values stored during calibration and determines whether ballast voltage adjustment is required. Ballast voltage adjustment is accomplished with an electronic switch array interfaced with zero-crossing opto-isolators 222 to the microcontroller output lines. Finally, if the system is not functioning properly, or cannot produce output power in the specified operating range, the microprocessor 200 activates the system status LED 112 to inform the user. The functional blocks of the electronic control system will now be described in greater detail.

According to a preferred embodiment of the present invention, a fully programmable embedded microcontroller 200 (e.g., Microchip PIC16F84) is provided that incorporates an arithmetic logic unit, system RAM, non-volatile storage RAM, ROM and interface circuitry into a single monolithic integrated circuit. The microcontroller 200 also contains an electronically independent "watch-dog" timer circuit which is programmed to reset the CPU in the event of a microcontroller hardware failure or a firmware execution error. The microcontroller 200 interfaces with the system sensors, the system status LED 112 and the electronic switch array via twelve programmable digital I/O lines. System calibration parameters are stored in the on-chip non-volatile RAM and all system firmware for controlling regulator functions is contained within the on-chip ROM storage. Firmware is programmed into ROM and verified using external programming hardware.

According to a preferred embodiment of the present invention, the visible light sensor 120 (e.g., a Texas Instruments TSL230B photosensor) is used to detect the tube output, and the output of the visible light sensor 120 is used as the regulation criterion. In the case of the TSL230B photosensor, a large area photodiode and an integrated current-to-frequency converter provide an output signal to the microcontroller as a series of digital pulses. The direct conversion of the optical signal to a digital format reduces circuit complexity and eliminates calibration and drift problems associated with analog circuitry.

The visible light sensor 120 is located behind the central tube 10(4) and the reflector panel 50 just to the left of center. In order to monitor the visible light contribution from multiple tubes, three slots 122(3)–122(5) are machined into the reflector 50 behind the central three tubes 10(3)–10(5). The cross sectional area and position of these slots 122(3) –122(5) are such that the visible light sensor 120 receives equally weighted inputs from the three bulbs 10(3)–10(5). According to a preferred embodiment of the present invention, the ratio of the cross-sectional areas for any two selected slots is proportional to the inverse squares of the selected slots' distances from the visible light sensor 120. The visible light sensor 120 is covered with a filter to match its spectral responsivity to that of the optometer which was used as the metering standard for calibration. Additionally, the visible light sensor 120 is covered with a glass diffuser to further minimize the positional dependence of the detector relative to the reflector slots 122(3)–122(5).

The voltage detection circuit 210 performs a dual function: it coordinates microcontroller operation with the system timer 100 and informs the microcontroller 200 when the maximum permissible ballast voltage has been reached. In a preferred embodiment of the present invention (referring to FIG. 9B), the voltage detection circuit 210 comprises a CD4046 CMOS phase lock loop (PLL) 214 used as a voltage controlled oscillator (VCO). A sample of the line voltage present on the ballast is rectified and used both to provide power to the CD4046 and to drive the VCO input. This arrangement enables the circuit to produce a digital pulse train whose frequency is proportional to ballast voltage. The pulse train is coupled via an opto-isolator 212 to the microcontroller 200 which determines the ballast voltage by measuring the pulse period.

Detection of system timer state is accomplished by placing the timer relay contacts in series with the ballast supply leads. When the timer 100 is off (e.g., no treatment), no voltage is present to drive either the voltage detection circuit 210 or the ballasts 20. Upon detecting this condition, the microcontroller 200 resets the system variables and loops until a pulse train (voltage) is present. Upon initiation of the timer countdown sequence, the timer relay contacts close, supplying voltage to the voltage detection circuit 210 and ballasts 20. When the presence of a pulse train is detected by the microcontroller 200, it commences regulation (see below). Although the regulator circuit can adjust the ballast voltage, treatment duration is hardware-controlled by the timer 100 through the series wiring of the relay contacts.

Once the visible light treatment has been initiated, the microcontroller 200 monitors the VCO pulse train and compares it with a value stored in memory during unit setup and calibration. If the measured value exceeds the stored value, further increases in ballast voltage are inhibited. The value stored in the microcontroller memory corresponds to the ballast voltage at one transformer tap setting less than its maximum rated operating voltage, preventing selection of a transformer tap setting that would exceed the maximum ballast voltage. This technique minimizes unnecessary switching and ensures that the ballast voltage does not exceed its maximum rated operating voltage (133 VAC in a preferred embodiment of the present invention) at any time.

Figure 9A:
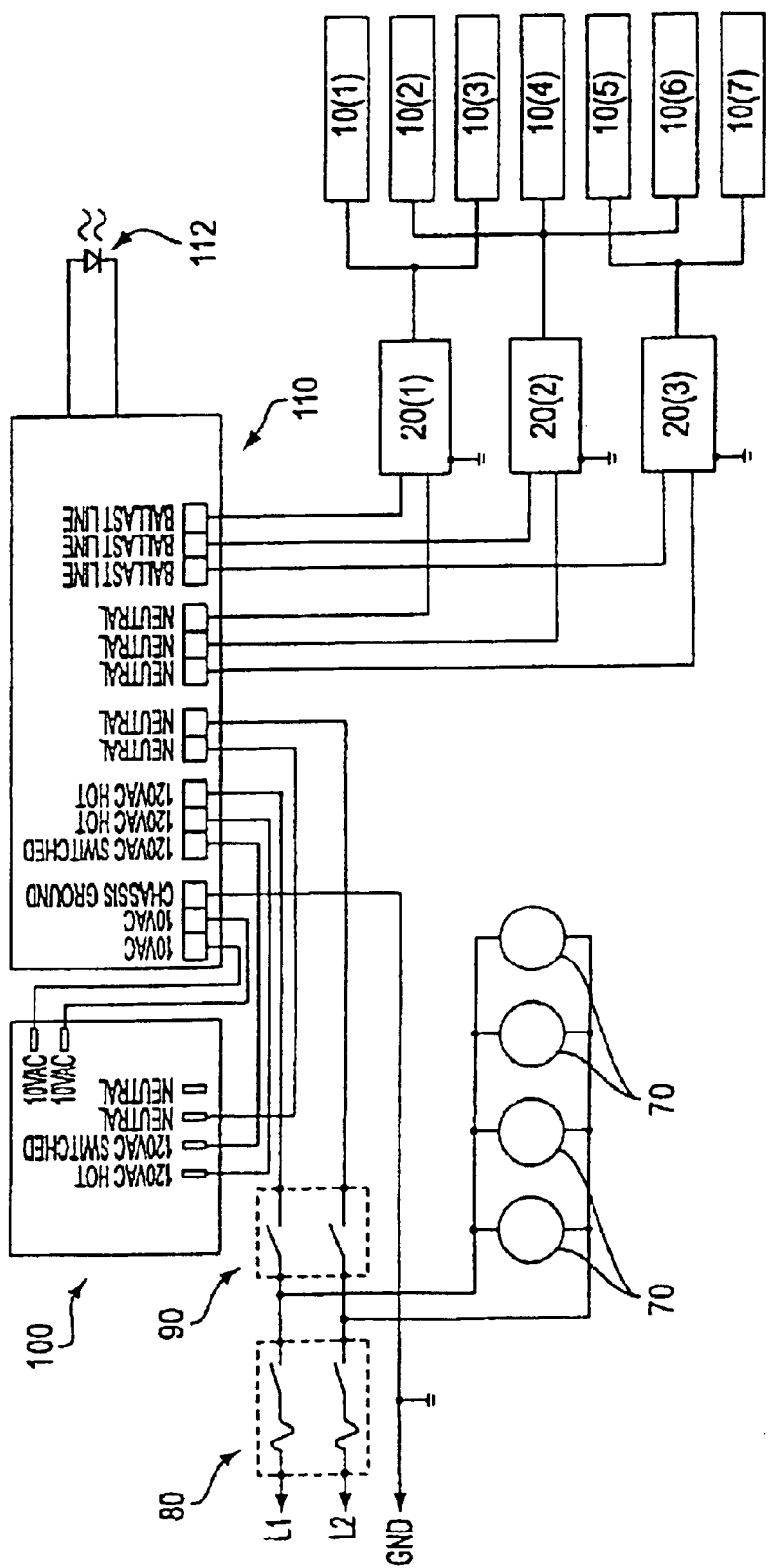
FIG. 9A is a schematic illustration of a modified wiring circuit of an illuminator according to the present invention.
Figure 9B:
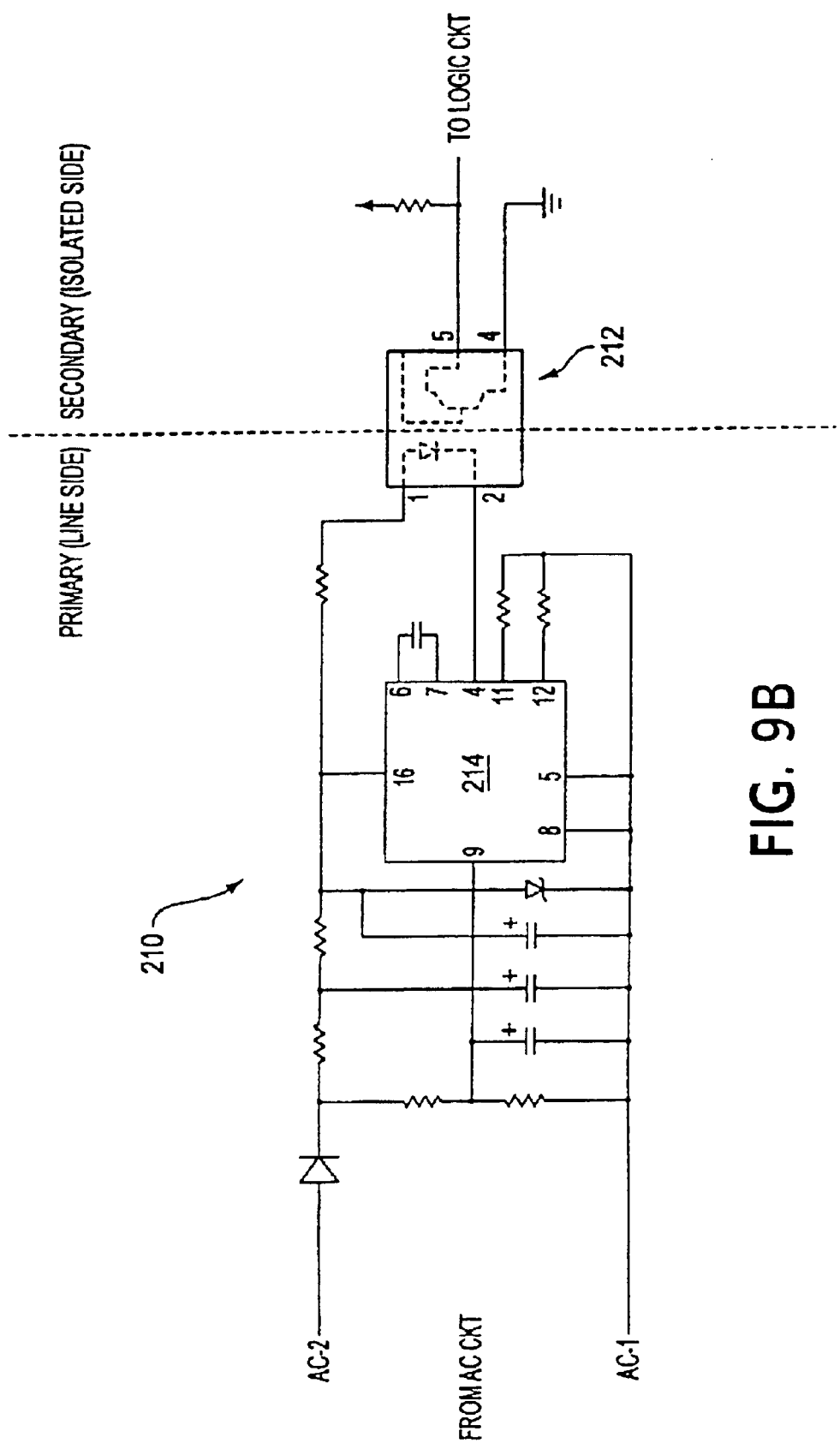
FIGS. 9B–9E are schematic illustrations showing details of the wiring circuit shown in FIG. 9A.
Figure 9C:
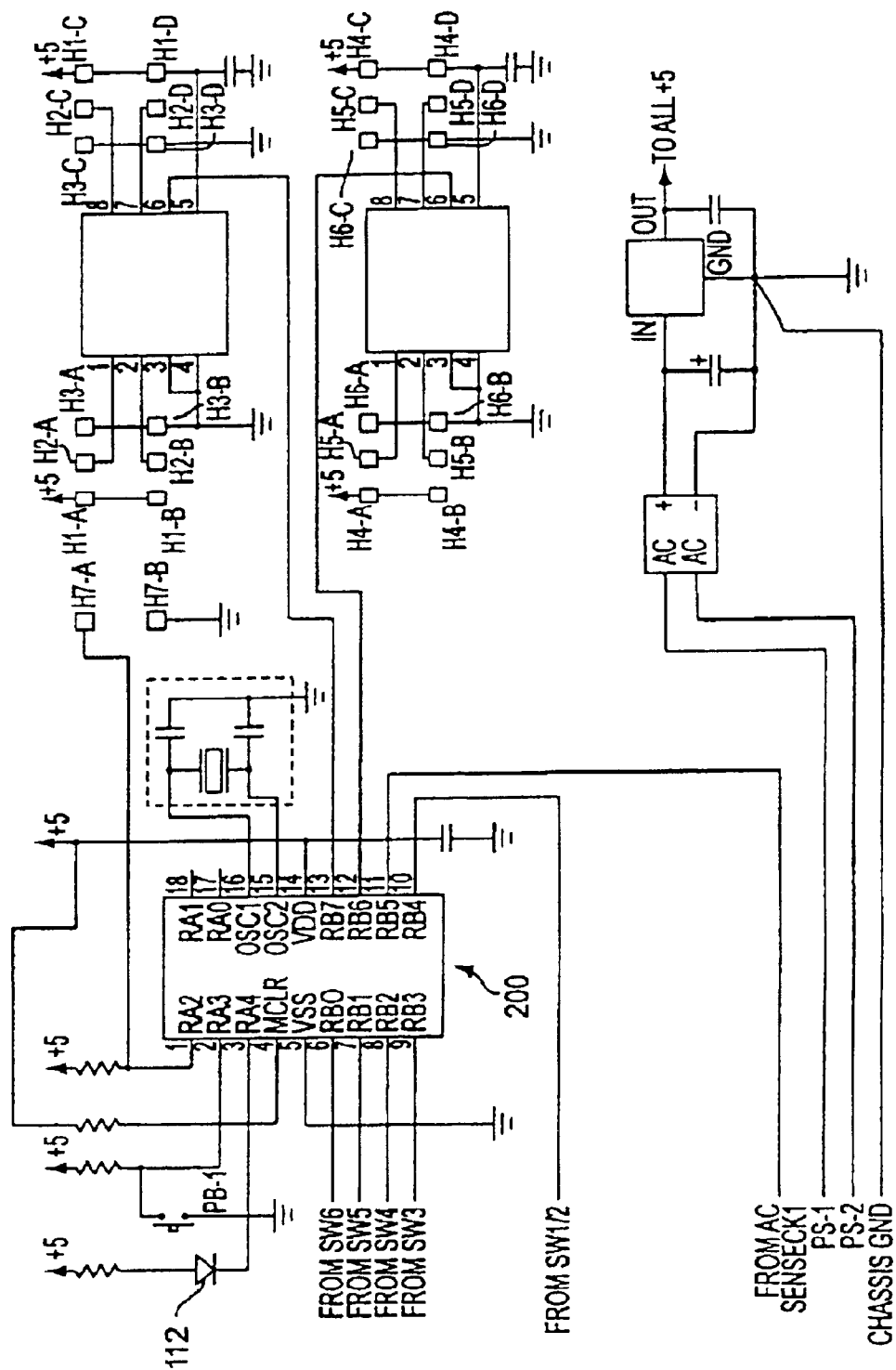
Figure 9D:
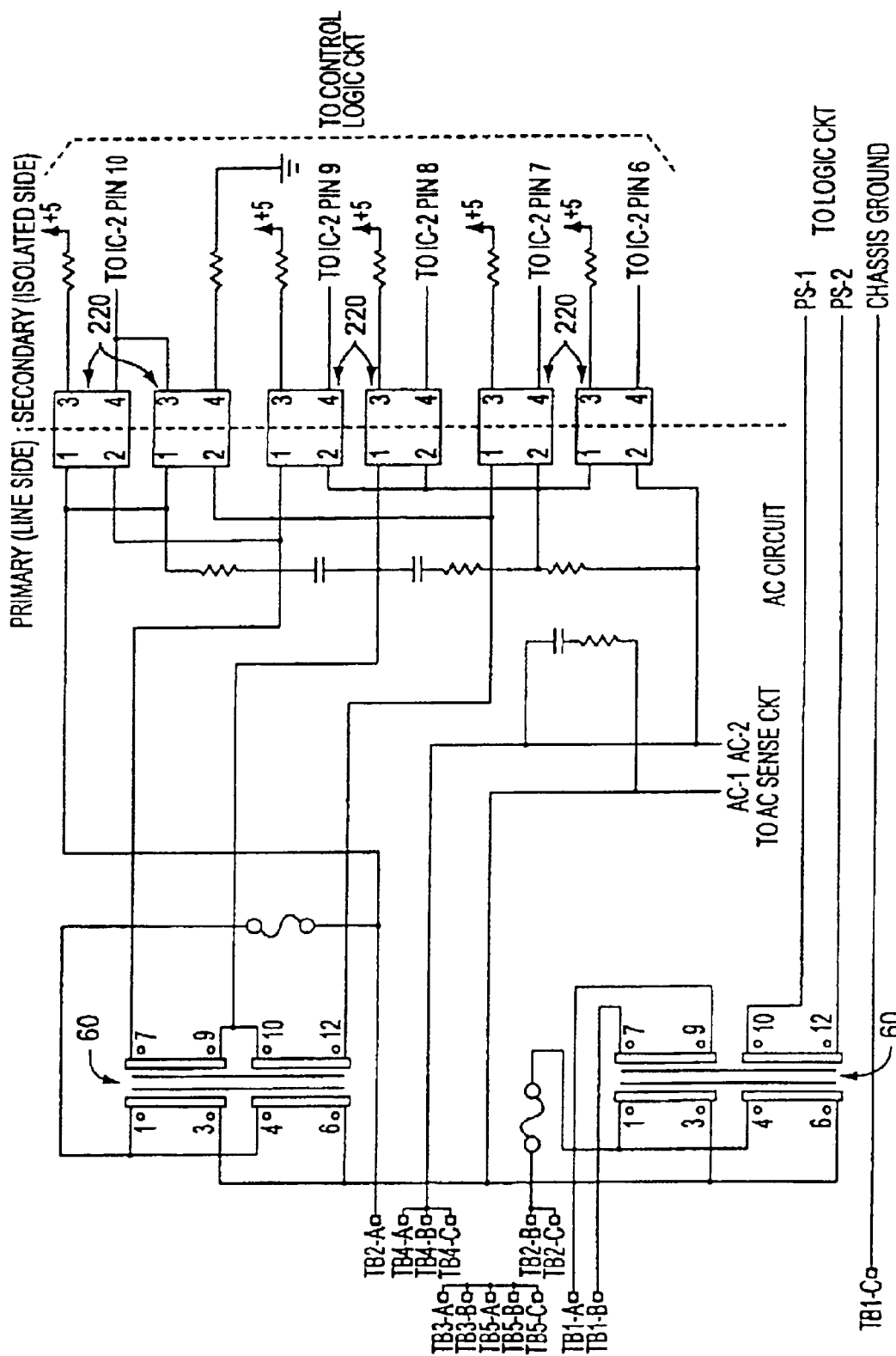
Figure 9E:
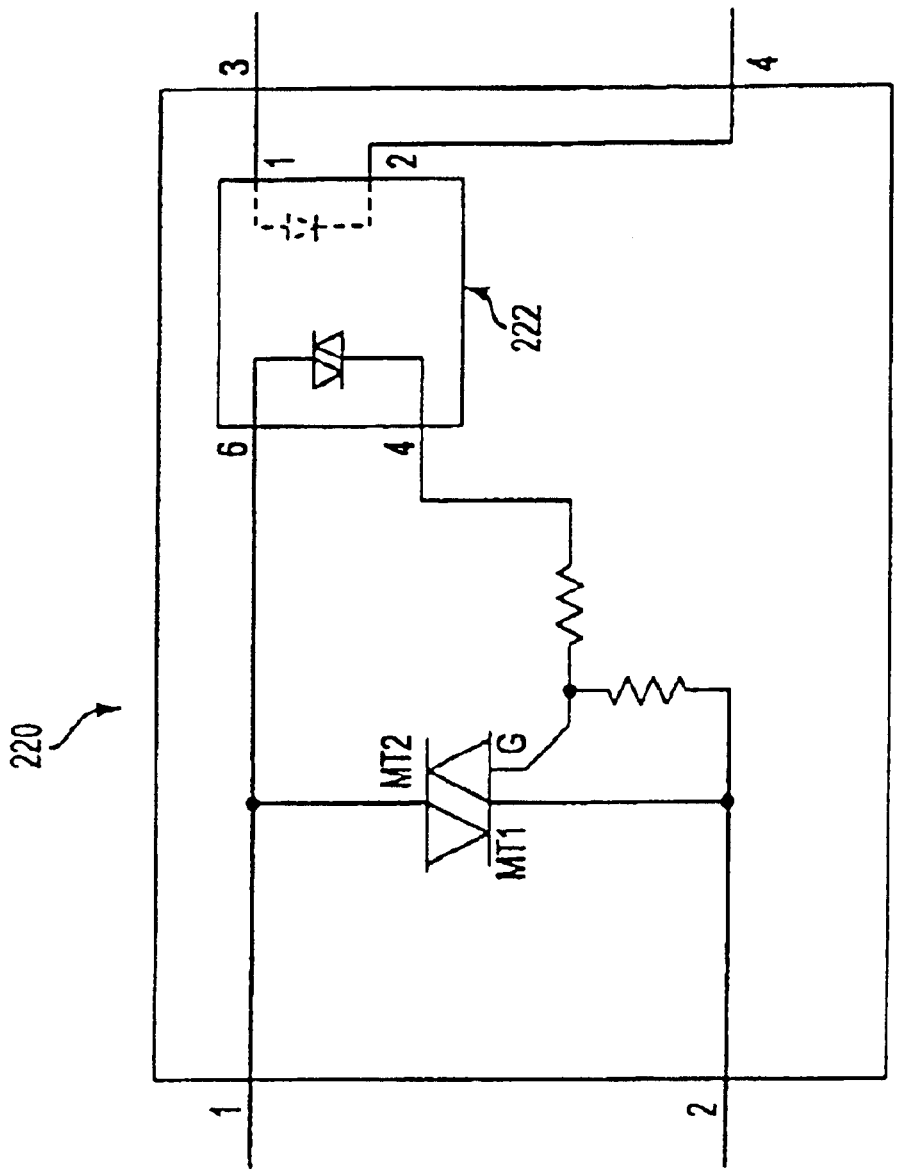

Referring to FIGS. 9D and 9E, the electronic switch array for transformer tap selection comprises six thyristor electronic switches 220 which connect the ballast input lines and the voltage selection taps on the buck/boost auto-transformers 60. The thyristor switches 220 control gates electro-optically coupled to the microcontroller 200. The microcontroller 200 thus increases or decreases the voltage applied to the ballasts 20 (increasing or decreasing the tube output) by energizing the appropriate control gates to select the appropriate taps.

According to preferred embodiments of the present invention, the system status indicator 112 shows when the output irradiance is not within specifications or when a control system failure has occurred. Inspection with a separate power meter is not necessary.

In one preferred embodiment of the present invention, the system status indicator 112 comprises a single LED which indicates the functional status of the system using a coded flash rate.

Immediately after the key is first turned to the "ON" position, the LED flashes three times to indicate that the system function is normal and is ready for use. If this fails to occur, either the LED or microcontroller is not functioning correctly, or the key switch 90 has been turned on, off, and on again too quickly for the microcontroller 200 to reset the LED control. If the LED does not flash three times after shutting off the power for several seconds and restarting it, the unit should not be used.

Rapid flashing immediately after the key switch 90 is turned on indicates there is a checksum error in the microcontroller 200. This occurs when a problem exists with the values stored in the microcontroller memory for the optical regulation and ballast voltage limits. In this instance, the unit is not operational and will not light.

If slow flashing occurs after timed treatment has been initiated, and the regulator attempts and fails 10 times to reduce the tube output to within the specified range, this indicates that the output may be too high and the ballast voltage cannot be further reduced. This may result from a microcontroller or component failure. If the LED slowly flashes during treatment, the treatment should be discontinued because the output power may be higher than the specified maximum.

If a steady glow occurs after timed treatment has been initiated, and the regulator attempts and fails 10 times to increase the tube output to within the specified range, this indicates that the output power may be too low and the ballast voltage cannot be further increased. If the LED glows steadily during treatment, but does not flash, the treatment may be continued, although the efficacy may be reduced as a result of low tube output. The LED will turn off if the output irradiance subsequently increases to above the minimum specified limit.

The microcontroller firmware has three main executable firmware modules: power-on setup, calibration and regulation. Only the power-on setup and the regulation modules execute during patient treatments.

The power-on setup module runs only at microcontroller power up when the key switch 90 is inserted and turned to "ON". At this time, the system variables are reset and calibration values stored in non-volatile RAM are retrieved. Additionally, a checksum calculation is performed and compared against a stored checksum. Any mismatch causes the firmware to shut down the system and initiate the LED rapid flashing code. Once successful startup has been achieved, control is transferred to the regulation module.

Upon entering the regulation module, the microcontroller 200 enters a voltage detection loop until it detects either a pulse train from the voltage circuit or contact closure on one of the technician-accessible service buttons/jumpers. The internal clock and the error flags are reset in this loop. If contact service closure is detected, control is transferred to the calibration module (see below). After the exposure time has been set on the timer 100 and the "START" button 104 has been pressed, the microcontroller 200 detects the pulse train produced by the VCO, and enters the main regulation loop. This starts the internal clock (independent of the timer). The main regulation loop reads the output of the VCO, the visible light sensor 120, and the internal clock; selects a new tap switch (if required); and displays any system errors every three seconds according to the algorithm described below. Loop execution continues until the timer terminates the treatment and the VCO pulse train.

When the timer countdown sequence is first initiated, the microcontroller 200 sets up the switch array to apply line voltage to the ballasts 20. During the first 2.5 minutes of the treatment (as determined from the internal clock), the visible light sensor 120 measures the tube output, and appropriate transformer taps are selected to keep the output irradiance between half the stored minimum and maximum regulation limits (9.3 and 10.7 mW/cm$^2$ according to a preferred embodiment of the present invention). This is done to provide optimum tube warm-up while maintaining output irradiance within the specified limits.

To allow sufficient time for the output to be within the required range at five minutes after any ballast voltage adjustment, the microcontroller 200 switches the minimum regulation limit to the stored value (9.3 mW/cm$^2$ in a preferred embodiment of the present invention) after the first two and a half minutes of operation; the maximum limit remains unchanged. Since the regulation limits are not modified beyond this point, the output irradiance will remain within these limits until treatment is terminated.

If the output cannot be maintained between the regulation limits, the system error flags activate the system status LED. A system error is not reported until the regulator has made ten attempts to correct the condition. This allows time for the tubes to respond to adjustment and to prevent "nuisance" error indications.

During each loop, the microcontroller 200 measures the ballast voltage via the VCO and sets an inhibit flag if the voltage is at maximum. While this action does not directly cause an error, one may be indicated if the system output is too low but cannot be raised due to the inhibit flag. If the timer 100 has terminated the treatment, the VCO pulse train is no longer present, and the microcontroller 200 returns to the voltage detection loop until a new treatment is initiated.

Data for the calibration module is established prior to clinical installation. The maximum allowable ballast voltage for the voltage detection circuit 210 and the visible light sensor 120 signals corresponding to the minimum and maximum regulation limits are programmed into the microcontroller memory using a setup/calibration algorithm.

To set the maximum ballast voltage, a voltage calibration jumper on the printed circuit board is shorted, causing the microcontroller 200 to enter the voltage calibration mode. A variac is used to adjust the ballast voltage to one transformer tap setting below the maximum allowable ballast voltage (127 VAC in a preferred embodiment of the present invention). Shorting the voltage calibration jumper a second time stores both this voltage value and a checksum in the microcontroller non-volatile memory. Each time the voltage calibration jumper is shorted, the system status LED flashes to indicate that the action has been completed.

Next, the maximum and minimum regulation limits are stored in the microcontroller memory by switching to the optical calibration mode. A reference UDT optometer (e.g., a UDT S370 power meter with a 247 detector/cosine diffuser assembly), is placed at a reference point. According to a preferred embodiment of the present invention, the reference point is 3" from the polycarbonate shield 40 at the center of the therapeutically active area. The ballast voltage is adjusted with a variac to obtain the desired maximum irradiance on the optometer. The corresponding output signal from the visible light sensor 120 is input to microcontroller memory as the maximum output limit. This procedure is repeated, adjusting the output to obtain the desired minimum irradiance on the optometer and setting the minimum limit of the regulator. Finally, a checksum is stored and the microcontroller 200 returns to the power-on setup module, commencing normal operation. As with the voltage calibration, the system status LED flashes each time calibration data has been stored.

It has been found that, according to a preferred embodiment of the present invention, the measured output over the active emitting area is within 70% of the measured maximum when measured with a cosine response detector at distances of 4" and 2", and within 60% of the measured maximum over all operation distances.

Exemplary Diagnosis and Treatment Methods

One example of a treatment method for pre-cancerous lesions, such as actinic keratosis, by PDT utilizing an illuminator described above in conjunction with 5-aminolevulinic acid (ALA) will now be described.

Essentially anhydrous ALA is admixed with a liquid diluent just prior to its use. The ALA admixture is topically applied to the lesions using a point applicator to control dispersion of the ALA admixture. A suitable applicator is described in U.S. patent application Ser. No. 08/962,294 (filed Oct. 31, 1997), and ALA is generally discussed further in U.S. patent application Ser. No. 08/921,664 (filed Sep. 2, 1997). The entire contents of these applications are incorporated herein by reference.

After the initial application of the ALA admixture has dried, one or more subsequent applications may be similarly applied. Approximately 2 mg/cm$^2$ of ALA is administered. Formation of photosensitive porphyrin and photosensitization of the treated lesions occurs over the next 14–18 hours, during which time exposure to direct sunlight or other bright light sources should be minimized. Between 14 and 18 hours after administration of the ALA, the lesions are irradiated by an illuminator according to the present invention. The illuminator irradiates the lesions with a uniform blue light for a prescribed period. According to a preferred treatment, the visible light has a nominal wavelength of 417 nm.

The invention thus provides a method for photodynamically diagnosing or treating a contoured surface of a patient which includes providing the illuminator described above, placing the patient in the illuminator, and illuminating the patient to diagnose or treat the patient. As described in the documents referred to above, the patient may be illuminated to treat actinic keratoses, acne, photo damaged skin, cancer, warts, or psoriasis. The method can also be used to remove hair and diagnose cancer.

Since total light Dose (J/cm$^2$)=Irradiance (W/cm$^2$)×Time (sec), the only additional parameter that needs to be controlled for delivery of the correct treatment light dose is exposure time. This is accomplished in a preferred embodiment of the present invention by the timer which controls electrical power to the ballasts and which can be set by the physician. Data has shown that 10 J/cm$^2$ delivered from a source with an irradiance density of 10 mW/cm$^2$ produces clinically acceptable results. From the equation above, this light dose will require an exposure time of 1000 seconds (16 min. 40 sec). A selected light dose may also be administered by additionally or alternatively varying the irradiance density.

Additional advantages and modifications will readily occur to those skilled in the art. Therefore, the invention in its broader aspects is not limited to the specific details, and representative devices, shown and described herein. Accordingly, various modifications may be made without departing from the spirit and scope of the general inventive concept as defined by the appended claims and their equivalents.

What is claimed is:

1. An illuminator for diagnosing or treating a contoured surface, the illuminator comprising:

an array of light sources supported by a housing, the array of light sources having a cross-section including an arc-shaped portion and configured to conform to a portion of a patient and to illuminate skin of the patient with light substantially entirely within the visible region, the housing defining an opening in said cross-section configured to permit relative movement between the patient and said array and configured to remain free of said light sources during illumination.

2. An illuminator as set forth in claim 1, wherein said array of light sources has a longitudinal axis and the opening is configured to permit said relative movement perpendicular to said longitudinal axis.

3. An illuminator as set forth in claim 1, wherein the illuminator is configured to illuminate the patient with substantially uniform intensity visible light.

4. An illuminator as set forth in claim 1, wherein said array is approximately U-shaped.

5. An illuminator as set forth in claim 1, wherein said housing is approximately U-shaped.

6. An illuminator as set forth in claim 1, wherein said array is configured to illuminate the face of the patient.

7. An illuminator as set forth in claim 1, wherein said array is configured to illuminate an upper portion of the patient while at the same time not illuminating a lower portion of the patient.

8. An illuminator as set forth in claim 1, wherein the array illuminates the patient with light substantially entirely within the blue region.

9. An illuminator as set forth in claim 1, wherein the light sources are curved.

10. An illuminator as set forth in claim 1, further comprising a reflector behind the light sources.

11. An illuminator as set forth in claim 1, wherein the housing comprises a central region and at least two arms extending from respective ends of the central region.

12. An illuminator as set forth in claim 1, further comprising a shield in front of the light sources.

13. An illuminator as set forth in claim 1, further comprising a sensor to monitor the light sources.

14. An illuminator as set forth in claim 1, further comprising an optical system for directing light from the light sources.

15. An illuminator as set forth in claim 1, wherein the housing comprises at least two arms.

16. A method for diagnosing or treating a contoured surface of a patient, comprising:

providing an illuminator having an array of light sources supported by a housing, the array of light sources having a cross-section including an arc-shaped portion and configured to conform to a portion of the patient and to illuminate skin of the patient with light substantially entirely within the visible region, the housing defining an opening in said cross-section configured to permit relative movement between the patient and said array and configured to remain free of said light sources during illumination; and placing a patient near said illuminator and illuminating the patient to diagnose or treat the patient.

17. A method as set forth in claim 16, wherein the patient is illuminated with light to treat actinic keratoses.

18. A method as set forth in claim 16, wherein the patient is illuminated with light to treat acne.

19. A method as set forth in claim 16, wherein the patient is illuminated with light to treat photo damaged skin.

20. A method as set forth in claim 16, wherein the patient is illuminated with light to remove hair.

21. A method as set forth in claim 16, wherein the patient is illuminated with light to diagnose cancer.

22. A method as set forth in claim 16, wherein the patient is illuminated with light to treat cancer.

23. A method as set forth in claim 16, wherein the patient is illuminated with light to treat warts.

24. A method as set forth in claim 16, wherein the patient is illuminated with light to treat psoriasis.

25. An illuminator as set forth in claim 6, wherein the light sources produce light having a peak intensity in the yellow region.

26. A method as set forth in claim 16, further comprising:
placing a patient near said illuminator and illuminating the patient to photodynamically diagnose or treat the patient.

* * * * *